United States Patent
Halbfinger et al.

(10) Patent No.: US 12,257,285 B2
(45) Date of Patent: *Mar. 25, 2025

(54) COMPOSITION OF BL-8040

(71) Applicants: BioLineRx Ltd., Modiln (IL); Biokine Therapeutics Ltd., Nes Ziona (IL)

(72) Inventors: Efrat Halbfinger, RaAnana (IL); Amnon Peled, Tel-Aviv (IL); Ella Sorani, Kadima (IL)

(73) Assignees: BioLineRx Ltd., Modiln (IL); Biokine Therapeutics Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/537,973

(22) Filed: Dec. 13, 2023

(65) Prior Publication Data

US 2024/0131111 A1    Apr. 25, 2024

Related U.S. Application Data

(63) Continuation of application No. 18/270,521, filed as application No. PCT/IL2021/051548 on Dec. 29, 2021.

(60) Provisional application No. 63/131,871, filed on Dec. 30, 2020.

(51) Int. Cl.
*A61K 38/12* (2006.01)
*A61P 35/00* (2006.01)

(52) U.S. Cl.
CPC ............. *A61K 38/12* (2013.01); *A61P 35/00* (2018.01)

(58) Field of Classification Search
CPC .................................................. A61K 38/12
USPC ....................................................... 514/19.9
See application file for complete search history.

(56) References Cited

U.S. PATENT DOCUMENTS

| | | | |
|---|---|---|---|
| 7,138,488 B2 | 11/2006 | Fujii et al. | |
| 7,423,007 B2 | 9/2008 | Fujii et al. | |
| 7,714,063 B2 | 5/2010 | Srivastava et al. | |
| 8,017,585 B2 | 9/2011 | Fujii et al. | |
| 8,435,939 B2 | 5/2013 | Fujii et al. | |
| 2006/0264378 A1 | 11/2006 | Fujii et al. | |
| 2013/0303460 A1 | 11/2013 | Pelled | |
| 2014/0294898 A1 | 10/2014 | Miller et al. | |

FOREIGN PATENT DOCUMENTS

| | | |
|---|---|---|
| EP | 1541585 | 6/2005 |
| WO | WO 2008/075369 | 6/2008 |
| WO | WO 2008/075370 | 6/2008 |
| WO | WO 2010/146578 | 12/2010 |
| WO | WO 2012/095849 | 7/2012 |
| WO | WO 2013/160895 | 10/2013 |
| WO | WO 2020/144111 | 7/2020 |
| WO | WO 2022/144885 | 7/2022 |
| WO | WO 2022/144886 | 7/2022 |

OTHER PUBLICATIONS

International Preliminary Report on Patentability Dated Jul. 13, 2023 From the International Bureau of WIPO Re. Application No. PCT/IL2021/051548 (12 Pages).
International Preliminary Report on Patentability Dated Jul. 13, 2023 From the International Bureau of WIPO Re. Application No. PCT/IL2021/051549 (7 Pages).
International Search Report and the Written Opinion Dated Mar. 14, 2022 From the International Searching Authority Re. Application No. PCT/IL2021/051548. (18 Pages).
International Search Report and the Written Opinion Dated Mar. 15, 2022 From the International Searching Authority Re. Application No. PCT/IL2021/051549. (13 Pages).
Abraham et al. "Enhanced Unique Pattern of Hematopoietic Cell Mobilization Induced by the CXCR4 Antagonist 4F-Benzoyl-TN14003", Stem Cells, 25(9): 2158-2166, Published Online May 24, 2007.
Martin et al. "Greening the Synthesis of Peptide Therapeutics: an Industrial Perspective", RSC Advances, 10: 42457-42492, Nov. 24, 2020.
Notice of Allowance Dated Feb. 7, 2024 from the US Patent and Trademark Office Re. U.S. Appl. No. 18/270,509. (10 pages).
Official Action Dated Jun. 10, 2024 from the US Patent and Trademark Office Re. U.S. Appl. No. 18/270,521. (22 pages).
Supplementary European Search Report and the European Search Opinion Dated Nov. 13, 2024 From the European Patent Office Re. Application No. 21914871.5. (8 Pages).
Supplementary European Search Report and the European Search Opinion Dated Oct. 23, 2024 From the European Patent Office Re. Application No. 21914872.3. (11 Pages).
Subirós-Funosas et al. "Oxyma: An Efficient Additive for Peptide Synthesis to Replace the Benzotriazole-Based HOBt and HOAt With A Lower Risk of Explosion", Chemistry, A European Journal, XP071829479, 15(37): 9394-9403, Sep. 21, 2009.
Grounds of Reason of Rejection Dated Jan. 17, 2024 From the Korean Intellectual Property Office Re. Application No. 10-2023-7026066 and Its Translation Into English. (5 Pages).
Notice of Reason(s) for Rejection Dated Jan. 21, 2024 From the Japan Patent Office Re. Application No. 2023-539883 and Its Translation Into English. (10 Pages).
ThermoFisher Scientific "Peptide Synthesis", Thermo Fisher Scientific, Internet Archive Wayback Machine, pp. 1-6, Retrieved online Jan. 9, 2025, Apr. 1, 2020.

*Primary Examiner* — Sean E Aeder

(57) ABSTRACT

A composition comprising BL-8040 (SEQ ID NO: 1) is disclosed herein, which may be for use in treating a condition treatable by BL-8040. The composition further comprises at least one compound characterized by a relative retention time of from 0.86 to 0.88 and/or a relative retention time of from 0.71 to 0.73 (wherein a relative retention time of BL-8040 is 1) under conditions described herein.

26 Claims, No Drawings
Specification includes a Sequence Listing.

COMPOSITION OF BL-8040

RELATED APPLICATIONS

This application is a Continuation of U.S. patent application Ser. No. 18/270,521 filed on Jun. 30, 2023, which is a National Phase of PCT Patent Application No. PCT/IL2021/051548 having International filing date of Dec. 29, 2021, which claims the benefit of priority under 35 USC § 119(e) of U.S. Provisional Patent Application No. 63/131,871 filed on Dec. 30, 2020. The contents of the above applications are all incorporated by reference as if fully set forth herein in their entirety.

SEQUENCE LISTING STATEMENT

The XML file, entitled 98797SequenceListing.xml, created on Dec. 11, 2023, comprising 10,627 bytes, submitted concurrently with the filing of this application is incorporated herein by reference.

FIELD AND BACKGROUND OF THE INVENTION

The present invention, in some embodiments thereof, relates to pharmaceutical products, and more particularly, but not exclusively, to novel compositions-of-matter comprising peptides such as BL-8040, which are usable, for example, in treating conditions such as cancer and/or arthritis, and processes for preparing same.

BL-8040 is a peptide also known as 4F-benzoyl-TN14003 (4-fluoro-benzoyl-Arg-Arg-Nal-Cys-Tyr-Cit-Lys-DLys-Pro-Tyr-Arg-Cit-Cys-Arg-$NH_2$, SEQ ID NO: 1), and is cyclic upon formation of a disulfide bond between the two Cys residues thereof.

U.S. Pat. No. 7,423,007 describes peptides having CXC4 antagonism; including 4F-benzoyl-TN14003. According to the teachings of U.S. Pat. No. 7,423,007, 4F-benzoyl-TN14003 is manufactured by solid phase synthesis using DIPCDI-HOBt as a coupling agent, in DMF (with amino acids added at 2.5 equivalents), followed by deprotection and cleavage using 1 M TMSBr-thioanisole/TFA with m-cresol and ethanedithiol, and cyclization by air oxidation.

Additional background art includes U.S. Pat. Nos. 7,138,488 and 8,435,939, and International Patent Application Publications WO 2008/075369, WO 2008/075370, WO 2010/146578, WO 2012/095849 and WO 2013/160895; and U.S. Provisional Patent Application No. 62/938,962.

SUMMARY OF THE INVENTION

According to an aspect of some embodiments of the invention, there is provided a composition-of-matter comprising BL-8040 (SEQ ID NO: 1) and at least one compound characterized by a relative retention time in a range of from 0.86 to 0.88, wherein the relative retention time is determined using a first mobile phase which is an aqueous solution of 0.017 M perchlorate at a pH in a range of from about 2.9 to about 3.3, a second mobile phase which is acetonitrile, a gradient whereby a concentration of the second mobile phase increases by about 10% in about 50 minutes from an initial concentration of about 20%, a C18 reverse phase column, an injection volume in a range of from about 5 to about 20 µl, and a flow rate of about 1 ml per minute, at a temperature of about 40° C., and wherein a relative retention time of BL-8040 (SEQ ID NO: 1) is defined as 1.

According to an aspect of some embodiments of the invention, there is provided a composition-of-matter comprising BL-8040 (SEQ ID NO: 1) and at least one compound characterized by a relative retention time in a range of from 0.86 to 0.88, wherein a total concentration ratio of the at least one compound to BL-8040 (SEQ ID NO: 1) is in a range of from 0.075% to 0.225% as determined according to absorption at a wavelength at about 226 nm, wherein the relative retention time is determined using a first mobile phase which is an aqueous solution of 0.017 M perchlorate at a pH in a range of from about 2.9 to about 3.3, a second mobile phase which is acetonitrile, a gradient whereby a concentration of the second mobile phase increases by about 10% in about 50 minutes from an initial concentration of about 20%, a C18 reverse phase column, an injection volume in a range of from about 5 to about 20 µl, and a flow rate of about 1 ml per minute, at a temperature of about 40° C., and wherein a relative retention time of BL-8040 (SEQ ID NO: 1) is defined as 1.

According to an aspect of some embodiments of the invention, there is provided a composition-of-matter comprising BL-8040 (SEQ ID NO: 1) and at least one compound characterized by a relative retention time in a range of from 0.71 to 0.73, the at least one compound representing at least 10% of all compounds other than BL-8040 (SEQ ID NO: 1) in the composition-of-matter as determined according to absorption at a wavelength at about 226 nm, wherein the relative retention time is determined using a first mobile phase which is an aqueous solution of 0.017 M perchlorate at a pH in a range of from about 2.9 to about 3.3, a second mobile phase which is acetonitrile, a gradient whereby a concentration of the second mobile phase increases by about 10% in about 50 minutes from an initial concentration of about 20%, a C18 reverse phase column, an injection volume in a range of from about 5 to about 20 µl, and a flow rate of about 1 ml per minute, at a temperature of about 40° C., and wherein a relative retention time of BL-8040 (SEQ ID NO: 1) is defined as 1.

According to an aspect of some embodiments of the present secret, there is provided a pharmaceutical composition comprising the composition-of-matter comprising BL-8040 (SEQ ID NO: 1) according to any of the respective embodiments described herein and any combination thereof, and a pharmaceutically acceptable carrier.

According to some of any of the embodiments relating to at least one compound characterized by a relative retention time in a range of from 0.86 to 0.88, the at least one compound characterized by a relative retention time in a range of from 0.86 to 0.88 represents at least 20% of all compounds other than BL-8040 (SEQ ID NO: 1) in the composition-of-matter as determined according to absorption at a wavelength at about 226 nm.

According to some of any of the embodiments relating to at least one compound characterized by a relative retention time in a range of from 0.86 to 0.88, the at least one compound characterized by a relative retention time in a range of from 0.86 to 0.88 represents at least 50% of all compounds other than BL-8040 (SEQ ID NO: 1) in the composition-of-matter as determined according to absorption at a wavelength at about 226 nm.

According to some of any of the embodiments relating to at least one compound characterized by a relative retention time in a range of from 0.86 to 0.88, the at least one compound characterized by a relative retention time in a range of from 0.86 to 0.88 comprises a compound having the same molecular weight as BL-8040 (SEQ ID NO: 1) and/or a compound having a molecular weight which is higher than the molecular weight of BL-8040 (SEQ ID NO: 1) by about 80 Da.

According to some of any of the embodiments relating to at least one compound characterized by a relative retention time in a range of from 0.86 to 0.88, a total concentration ratio of the at least one compound characterized by a relative retention time in a range of from 0.86 to 0.88 to BL-8040 (SEQ ID NO: 1) is at least about 0.01%, optionally at least about 0.05%.

According to some of any of the embodiments relating to at least one compound characterized by a relative retention time in a range of from 0.86 to 0.88, a total concentration ratio of the at least one compound characterized by a relative retention time in a range of from 0.86 to 0.88 to BL-8040 (SEQ ID NO: 1) is no more than about 1%.

According to some of any of the embodiments relating to at least one compound characterized by a relative retention time in a range of from 0.86 to 0.88, a total concentration ratio of the at least one compound characterized by a relative retention time in a range of from 0.86 to 0.88 to BL-8040 (SEQ ID NO: 1) is in a range of from about 0.075% to about 0.225%.

According to some of any of the embodiments relating to at least one compound characterized by a relative retention time in a range of from 0.86 to 0.88, a total concentration ratio of the at least one compound characterized by a relative retention time in a range of from 0.86 to 0.88 to BL-8040 (SEQ ID NO: 1) is in a range of from about 0.1% to about 0.2%.

According to some of any of the embodiments relating to at least one compound characterized by a relative retention time in a range of from 0.86 to 0.88, a concentration of cyclic deamidated BL-8040 (SEQ ID NO: 2) in the composition-of-matter is no more than 50% of a total concentration of the at least one compound characterized by a relative retention time in a range of from 0.86 to 0.88.

According to some of any of the embodiments relating to at least one compound characterized by a relative retention time in a range of from 0.86 to 0.88, a concentration of cyclic D-Lys(Ac) BL-8040 (SEQ ID NO: 3) in the composition-of-matter is no more than 50% of a total concentration of the at least one compound characterized by a relative retention time in a range of from 0.86 to 0.88.

According to some of any of the embodiments relating to at least one compound characterized by a relative retention time in a range of from 0.86 to 0.88, a total concentration of cyclic deamidated BL-8040 (SEQ ID NO: 2) and cyclic D-Lys(Ac) BL-8040 (SEQ ID NO: 3) in the composition-of-matter is no more than 80% of a total concentration of the at least one compound characterized by a relative retention time in a range of from 0.86 to 0.88.

According to some of any of the embodiments described herein relating to at least one compound characterized by a relative retention time in a range of from 0.86 to 0.88, the composition-of-matter further comprises at least one compound characterized by a relative retention time in a range of from 0.71 to 0.73 according to any of the respective embodiments described herein.

According to some of any of the embodiments described herein relating to at least one compound characterized by a relative retention time in a range of from 0.71 to 0.73, the at least one compound characterized by a relative retention time in a range of from 0.71 to 0.73 represents at least 10% of all compounds other than BL-8040 (SEQ ID NO: 1) in the composition-of-matter as determined according to absorption at a wavelength at about 226 nm.

According to some of any of the embodiments described herein relating to at least one compound characterized by a relative retention time in a range of from 0.71 to 0.73, a total concentration ratio of the at least one compound characterized by a relative retention time in a range of from 0.71 to 0.73 to BL-8040 (SEQ ID NO: 1) is at least about 0.01%.

According to some of any of the embodiments described herein relating to at least one compound characterized by a relative retention time in a range of from 0.71 to 0.73, a total concentration ratio of the at least one compound characterized by a relative retention time in a range of from 0.71 to 0.73 to BL-8040 (SEQ ID NO: 1) is no more than about 0.5%.

According to some of any of the embodiments described herein relating to at least one compound characterized by a relative retention time in a range of from 0.71 to 0.73, a total concentration ratio of the at least one compound characterized by a relative retention time in a range of from 0.71 to 0.73 to BL-8040 (SEQ ID NO: 1) is in a range of from about 0.03% to about 0.15%.

According to some of any of the embodiments described herein relating to at least one compound characterized by a relative retention time in a range of from 0.71 to 0.73, a concentration of cyclic deamidated BL-8040 (SEQ ID NO: 2) in the composition-of-matter is no more than a total concentration of the at least one compound characterized by a relative retention time in a range of from 0.71 to 0.73.

According to some of any of the embodiments described herein relating to at least one compound characterized by a relative retention time in a range of from 0.71 to 0.73, a concentration of cyclic D-Lys(Ac) BL-8040 (SEQ ID NO: 3) in the composition-of-matter is no more than a total concentration of the at least one compound characterized by a relative retention time in a range of from 0.71 to 0.73.

According to some of any of the embodiments described herein relating to at least one compound characterized by a relative retention time in a range of from 0.71 to 0.73, a total concentration of cyclic deamidated BL-8040 (SEQ ID NO: 2) and cyclic D-Lys(Ac) BL-8040 (SEQ ID NO: 3) in the composition-of-matter is no more than 150% of a total concentration of the at least one compound characterized by a relative retention time in a range of from 0.71 to 0.73.

According to some of any of the embodiments described herein relating to at least one compound characterized by a relative retention time in a range of from 0.71 to 0.73, the composition-of-matter further comprises at least one compound characterized by a relative retention time in a range of from 0.86 to 0.88 according to any of the respective embodiments described herein.

According to some of any of the embodiments described herein relating to at least one compound characterized by a relative retention time in a range of from 0.71 to 0.73 and/or to at least one compound characterized by a relative retention time in a range of from 0.86 to 0.88, and any combination thereof, a total concentration of the at least one compound characterized by a relative retention time in a range of from 0.86 to 0.88 and the at least one compound characterized by a relative retention time in a range of from 0.71 to 0.73 represents at least 50% of all compounds other than BL-8040 (SEQ ID NO: 1) in the composition-of-matter as determined according to absorption at a wavelength at about 226 nm.

According to some of any of the embodiments, the reverse phase column is characterized by at least one of: a length of about 250 mm length, an inner diameter of about 4.6 mm, and a particle size of about 5 μm.

According to some of any of the embodiments, the composition-of-matter is characterized by at least two of, and optionally at least three of:
(i) enhanced promotion of in vivo neutrophil migration to peripheral blood;
(ii) enhanced inhibition of in vitro CXCL12-induced migration of breast cancer cells;
(iii) enhanced inhibition of in vitro CXCL12-induced migration of T-cell-derived leukemia cells;
(iv) enhanced inhibition of metastatic breast cancer cell migration to lungs in an animal model;
(v) enhanced inhibition of delayed-type hypersensitivity in an animal model;
(vi) enhanced inhibition of collagen-induced arthritis in an animal model; and
(vii) enhanced inhibition of binding of CXCL12 to CXCR4 in cells in vitro,
relative to a corresponding composition-of-matter lacking the at least one compound characterized by a relative retention time in a range of from 0.71 to 0.73 and the at least one compound characterized by a relative retention time in a range of from 0.86 to 0.88.

According to some of any of the embodiments, the composition-of-matter is characterized by enhanced promotion of in vivo neutrophil migration to peripheral blood, relative to a corresponding composition-of-matter lacking the at least one compound characterized by a relative retention time in a range of from 0.71 to 0.73 and the at least one compound characterized by a relative retention time in a range of from 0.86 to 0.88.

According to some of any of the embodiments described herein, the composition-of-matter is obtainable by a process comprising:
(a) sequentially coupling amino acids and 4-fluorobenzoic acid to a resin by solid phase peptide synthesis, thereby obtaining a linear peptide coupled to the resin;
(b) cleaving the linear peptide from the resin, thereby obtaining a free linear peptide;
(c) oxidizing cysteine residues of the linear peptide to form an intramolecular disulfide bond, thereby obtaining the cyclic peptide having SEQ ID NO: 1 in solution; and
(d) isolating the cyclic peptide having SEQ ID NO: 1, or a pharmaceutically acceptable salt thereof,
wherein:
(i) the coupling is effected using diisopropylcarbodiimide (DIC) in combination with ethyl cyanohydroxyiminoacetate and/or N-hydroxybenzotriazole;
(ii) the cleaving is effected by contacting the linear peptide coupled to the resin with a solution comprising trifluoroacetic acid (TFA) and a scavenger selected from the group consisting of dithioerythritol (DTE) and dithiothreitol (DTT);
(iii) the process further comprises precipitating the free linear peptide after the cleaving without concentrating the free linear peptide by evaporation prior to the precipitating;
(iv) the contacting is effected by contacting an aqueous solution comprising the linear peptide at a concentration of at least 5 mg/mL with hydrogen peroxide;
(v) the isolating comprises loading the cyclic peptide on a reverse phase chromatography column at a concentration of no more than 40 grams cyclic peptide per kg of the column, and eluting the cyclic peptide from the column;
(vi) the isolating the cyclic peptide having SEQ ID NO: 1 comprises lyophilization, and the process further comprises grinding the cyclic peptide following the lyophilization; and/or
(vii) a degree of substitution of the resin is at least 0.3 milliequivalents per gram, and/or the resin is a Rink aminomethylstyrene (AMS) resin.

According to some of any of the embodiments described herein relating to a composition-of-matter, the composition-of-matter is for use in the treatment of a condition treatable by BL-8040 (SEQ ID NO: 1).

According to some of any of the embodiments described herein relating to a composition-of-matter, the composition-of-matter is for use in the treatment of a condition in which inhibiting CXCR4 is advantageous.

According to some of any of the embodiments described herein relating to a composition-of-matter, the composition-of-matter is for use in the treatment of a condition selected from the group consisting of retinoblastoma, neuroectodermal derived tumors, large cell lung cancer, multiple myeloma, microglioma, glioma, breast cancer, pancreatic cancer, thrombocytopenia, risk of bone marrow suppression, and HIV infection.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS
OF THE INVENTION

The present invention, in some embodiments thereof, relates to pharmaceutical products, and more particularly, but not exclusively, to novel compositions-of-matter comprising peptides such as BL-8040 (SEQ ID NO: 1), which are usable, for example, in treating conditions such as cancer and/or arthritis, and processes for preparing same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Following laborious experimentation, the inventor has uncovered novel compositions-of-matter comprising BL-8040 (SEQ ID NO: 1) peptide with advantageous biological activity, which may advantageously be prepared in large-scale syntheses of the peptide, while also being suitable for preparation formulations for pharmaceutical administration.

According to an aspect of some embodiments of the invention, there is provided a composition-of-matter comprising BL-8040 (SEQ ID NO: 1) and at least one compound characterized by a relative retention time in a range of from 0.86 to 0.88 and/or at least one compound characterized by a relative retention time in a range of from 0.71 to 0.73, as determined according to any of the embodiments described herein relating to relative retention time.

Herein throughout, the term "BL-8040" refers to a cyclic peptide having SEQ ID NO: 1.

Herein, a "cyclic" peptide refers to a peptide comprising a pair of cysteine residues linked by a disulfide bond. For example, "cyclic peptide having SEQ ID NO: 1" refers to SEQ ID NO: 1 in which the two cysteine residues thereof are linked by a disulfide bond.

According to some of any of the embodiments described herein, the composition-of-matter comprises at least one compound characterized by a relative retention time in a range of from 0.86 to 0.88, according to any of the respective embodiments described herein (e.g., in an amount according to any of the respective embodiments described herein). In some such embodiments, the relative retention time of the at least one compound is in a range of from 0.865 to 0.88. In some embodiments, the relative retention time is in a range of from 0.868 to 0.878. In some embodiments, the relative retention time is in a range of from 0.870 to 0.876.

According to some of any of the embodiments described herein, the composition-of-matter comprises at least one compound characterized by a relative retention time in a range of from 0.71 to 0.73, according to any of the respective embodiments described herein (e.g., in an amount according to any of the respective embodiments described herein). In some such embodiments, the relative retention time of the at least one compound is in a range of from 0.715 to 0.73. In some embodiments, the relative retention time is in a range of from 0.718 to 0.728. In some embodiments, the relative retention time is in a range of from 0.719 to 0.726.

According to some of any of the embodiments described herein, the composition-of-matter comprises both at least one compound characterized by a relative retention time in a range of from 0.86 to 0.88, according to any of the respective embodiments described herein (e.g., in an amount according to any of the respective embodiments described herein) and at least one compound characterized by a relative retention time in a range of from 0.71 to 0.73, according to any of the respective embodiments described herein (e.g., in an amount according to any of the respective embodiments described herein).

Herein throughout, whenever a range of from 0.86 to 0.88 or from 0.71 to 0.73 is indicated, the range encompasses a range of from 0.860 to 0.880 or from 0.710 to 0.730, respectively, as well as any intermediate values (which may serve as an upper limit or lower limit) and subranges therebetween.

Herein, the term "relative retention time" refers to a retention time of a compound (e.g., a component of a composition-of-matter described herein) when performing high performance liquid chromatography (HPLC) relative to a retention time (under the same conditions) of a reference compound, which herein is BL-8040 (SEQ ID NO: 1). Thus, the relative retention time of BL-8040 (SEQ ID NO: 1) is by definition equal to 1.

In addition, the term "relative retention time" is determined according to the time at which the greatest concentration of compound is retained (e.g., the mode). Thus, for example, a compound defined as having a retention time of 0.87 may include individual molecules exiting a chromatography column at a retention time ranging from 0.84 to 0.90 (e.g., in a bell curve distribution). However, the retention time of all molecules of such a compound will be considered as being 0.87, and therefore "in a range of from 0.86 to 0.88".

The relative retention time is preferably determined using a C18 reverse phase column, optionally a silica-based C18 column (e.g., a Hypersil Gold™ C18 column). In some of any of the embodiments described herein, the reverse phase column is characterized by at least one of, at least two of, or all of the following features: a length of about 250 mm length, an inner diameter of about 4.6 mm, and a particle size of about 5 μm.

The relative retention time according to any of the respective embodiments described herein is preferably determined using an aqueous solution of about 0.017 M perchlorate at a pH in a range of from about 3.0 to about 3.3 as a first mobile phase which is, acetonitrile as a second mobile phase, and a gradient whereby a concentration of the second mobile phase increases by about 10% (e.g., by 10.0%) in about 50 minutes from an initial concentration of about 20% (e.g., increasing from 19.3% to 29.3% or from 20% to 30%).

Relative retention time is preferably determined at a temperature of about 40° C., an injection volume in a range of from about 5 to about 20 μl, and a flow rate of about 1 ml per minute. Detection of compounds may optionally be effected by determining absorption at a wavelength of about 226 nm. In exemplary embodiments, an Agilent™ 1200 or Agilent™ 1100 HPLC system is used.

A compound in a composition-of-matter characterized by an indicated relative retention time (according to any of the respective embodiments described herein) may optionally be present in a concentration which is at least about 0.01% of the concentration of the BL-8040 (SEQ ID NO: 1), as determined according to absorption at a wavelength at about 226 nm.

Herein, the phrase "as determined according to absorption" means that a relative concentration of compound (e.g., in calculating a percentage described herein) is determined by quantification of absorption (e.g., optical density) at a given wavelength (e.g., 226 nm). Thus, for example, two fractions (e.g., representing two different compounds in a composition-of-matter) would be considered as having the same concentration of compound if they absorb to the same degree, regardless of whether they contain the same concentration of molecules of the compound(s); and a compound which does not absorb at all at the indicated wavelength would be considered as having a concentration of zero.

In some of any of the embodiments described herein, the composition-of-matter is characterized by a relatively low amount of compounds other than BL-8040 (SEQ ID NO: 1) and the at least one compound characterized by a relative retention time of 0.71 to 0.73 and/or 0.86 to 0.88 (according to any of the respective embodiments described herein), e.g., such that the at least one compound characterized by a relative retention time of 0.71 to 0.73 and/or 0.86 to 0.88 represents a relatively large proportion (e.g., as determined according to absorption at a wavelength at about 226 nm, as defined herein) of all compounds other than BL-8040 (SEQ ID NO: 1).

Herein, the term "all compounds other than BL-8040" refers to a sum of compounds in a composition-of-matter described herein which are not BL-8040 (SEQ ID NO: 1), a counter-ion thereof, or a solvent (e.g., buffered aqueous solution). The compounds other than BL-8040 (SEQ ID NO: 1) may include, for example, compounds differing in chemical composition and/or molecular configuration (e.g., stereoisomers of BL-8040 (SEQ ID NO: 1)). It is to be appreciated that some compounds which are not BL-8040 (SEQ ID NO: 1) may fail to absorb at an indicated wavelength, and thus fail to contribute substantially to "all compounds other than BL-8040" as determined according to absorption (as defined herein).

In some of any of the respective embodiments described herein, the term "all compounds other than BL-8040" includes only compounds having a relative retention time of at least 0.1, optionally from 0.1 to 2, as determined under conditions described herein; that is, compounds having a relative retention time outside the indicated range are in such embodiments excluded (e.g., for convenience of measurement) from the definition of "compounds other than BL-8040" (according to any of the respective embodiments described herein), even if they are not a counter-ion or solvent. In some embodiments, the term "all compounds other than BL-8040" includes only compounds having a relative retention time of at least 0.5, optionally from 0.5 to 1.5.

In some of any of the respective embodiments described herein, the term "all compounds other than BL-8040" refers to the sum of peptide compounds other than BL-8040 (SEQ ID NO: 1); that is, compounds which are not peptides (i.e., compounds which do not include at least two amino acid residues linked by an amide bond) are in such embodiments excluded from the definition of "compounds other than BL-8040" (according to any of the respective embodiments described herein), even if they have the indicated relative retention time.

Without being bound by any particular theory, it is believed that peptides, by nature, which are somewhat similar to BL-8040 (SEQ ID NO: 1), may come in a wide variety of variants (e.g., one or more amino acid residue(s) in a peptide may independently be substituted, degraded and/or replaced by another residue, such as a stereoisomer thereof), some of which may provide an advantageous activity, whereas non-peptide compounds are unlikely to provide an advantageous activity and are therefore of less interest.

According to some of any of the embodiments, the at least one compound characterized by a relative retention time in a range of from 0.86 to 0.88 (according to any of the respective embodiments described herein) comprises a compound having the same molecular weight as BL-8040 (SEQ ID NO: 1) and/or a compound having a molecular weight which is higher than the molecular weight of BL-8040 (SEQ ID NO: 1) by no more than 100 Da, e.g., by about 80 Da. As exemplified herein, the molecular weight of a compound may be determined by mass spectrometry, optionally using liquid chromatography-mass spectrometry, according to techniques known in the art.

According to some of any of the embodiments, the at least one compound characterized by a relative retention time in a range of from 0.86 to 0.88 (according to any of the respective embodiments described herein) consists of one or more compounds having the same molecular weight as BL-8040 (SEQ ID NO: 1) and/or one or more compounds having a molecular weight which is higher than the molecular weight of BL-8040 (SEQ ID NO: 1) by about 80 Da; that is, compounds which do not have the aforementioned molecular weight are in such embodiments excluded from the definition of "at least one compound characterized by a relative retention time in a range of from 0.86 to 0.88" (according to any of the respective embodiments described herein), even if they have the indicated relative retention time. In some such embodiments, the at least one at least one compound characterized by a relative retention time in a range of from 0.86 to 0.88 consists of one or more compounds having the same molecular weight as BL-8040 (SEQ ID NO: 1).

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is at least about 0.01%. In some such embodiments, the total concentration ratio is at least about 0.02%. In some embodiments, the total concentration ratio is at least about 0.03%. In some embodiments, the total concentration ratio is at least about 0.05%. In some embodiments, the total concentration ratio is at least about 0.075%. In some embodiments, the total concentration ratio is at least about 0.1%. In some embodiments, the total concentration ratio is at least about 0.2%. In some embodiments, the total concentration ratio is at least about 0.3%. In some embodiments, the total concentration ratio is at least about 0.4%. In some embodiments, the total concentration ratio is at least about 0.5%.

Herein the term "total concentration ratio" refers to a ratio of a total concentration of (one or more) compounds (e.g., compounds having a relative retention rate within an indicated range according to any of the respective embodiments described herein) to another concentration (e.g., a concentration of BL-8040 (SEQ ID NO: 1)), which represents unity (or 100% when the ratio is defined as a percentage); wherein the concentrations are determined by absorption as defined herein.

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is no more than about 1%. In some such embodiments, the total concentration ratio is in a range of from 0.01% to 1%. In some embodiments, the total concentration ratio is in a range of from 0.02% to 1%. In some embodiments, the total concentration ratio is in a range of from 0.03% to 1%. In some embodiments, the total concentration ratio is in a range of from 0.05% to 1%. In some embodiments, the total concentration ratio is in a range of from 0.075% to 1%. In some embodiments, the total concentration ratio is in a range of from 0.1% to 1%. In some embodiments, the total concentration ratio is in a range of from 0.2% to 1%. In some embodiments, the total concentration ratio is in a range of from 0.3% to 1%. In some embodiments, the total concentration ratio is in a range of from 0.4% to 1%. In some embodiments, the total concentration ratio is in a range of from 0.5% to 1%.

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is no more than about 0.5%. In some such embodiments, the total concentration ratio is in a range of from 0.01% to 0.5%. In some embodiments, the total concentration ratio is in a range of from 0.02% to 0.5%. In some embodiments, the total concentration ratio is in a range of from 0.03% to 0.5%. In some embodiments, the total concentration ratio is in a range of from 0.05% to 0.5%. In some embodiments, the total concentration ratio is in a range of from 0.075% to 0.5%. In some embodiments, the total concentration ratio is in a range of from 0.1% to 0.5%. In some embodiments, the total concentration ratio is in a range of from 0.2% to 0.5%. In some embodiments, the total concentration ratio is in a range of from 0.3% to 0.5%.

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is no more than about 0.3%. In some such embodiments, the total concentration ratio is in a range of from 0.01% to 0.3%. In some embodiments, the total concentration ratio is in a range of from 0.02% to 0.3%. In some embodiments, the total concentration ratio is in a range of from 0.03% to 0.3%. In some embodiments, the total concentration ratio is in a range of from 0.05% to 0.3%. In some embodiments, the total concentration ratio is in a range of from 0.075% to 0.3%. In some embodiments, the total concentration ratio is in a range of from 0.1% to 0.3%. In some embodiments, the total concentration ratio is in a range of from 0.2% to 0.3%.

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is no more than about 0.25%. In some such embodiments, the total concentration ratio is in a range of from 0.01% to 0.25%. In some embodiments, the total concentration ratio is in a range of from 0.02% to 0.25%. In some embodiments, the total concentration ratio is in a range of from 0.03% to 0.25%. In some embodiments, the total concentration ratio is in a range of from 0.05% to 0.25%. In some embodiments, the total concentration ratio is in a range of from 0.075% to 0.25%. In some embodiments, the total concentration ratio is in a range of from 0.1% to 0.25%.

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is no more than about 0.2%. In some such embodiments, the total concentration ratio is in a range of from 0.01% to 0.2%. In some embodiments, the total concentration ratio is in a range of from 0.02% to 0.2%. In some embodiments, the total concentration ratio is in a range of from 0.03% to 0.2%. In some embodiments, the total concentration ratio is in a range of from 0.05% to 0.2%. In some embodiments, the total concentration ratio is in a range of from 0.075% to 0.2%.

In some of any of the embodiments described herein, a total concentration ratio of the at least one compound characterized by a relative retention time in a range of from 0.86 to 0.88 (according to any of the embodiments described herein) to BL-8040 (SEQ ID NO: 1) is in a range of from about 0.075% to about 0.225%. In some such embodiments, the total concentration ratio is in a range of from 0.1% to 0.2%.

In some of any of the embodiments described herein, the at least one compound characterized by a relative retention time in a range of from 0.86 to 0.88 (according to any of the embodiments described herein) represents at least 20% of all compounds other than BL-8040 (SEQ ID NO: 1) in the composition-of-matter as determined according to absorption at a wavelength at about 226 nm (as defined herein); that is, at least 20% of all compounds other than BL-8040 (SEQ ID NO: 1) (determined as described herein) are characterized by a relative retention time in the indicated range (e.g., from 0.86 to 0.88). In some such embodiments, the at least one compound characterized by a relative retention time in a range of from 0.86 to 0.88 represents at least 30% of all compounds other than BL-8040 (SEQ ID NO: 1) in the composition-of-matter (determined as described herein). In some embodiments, the at least one compound characterized by a relative retention time in a range of from 0.86 to 0.88 represents at least 40% of all compounds other than BL-8040 (SEQ ID NO: 1) in the composition-of-matter (determined as described herein). In some embodiments, the at least one compound characterized by a relative retention time in a range of from 0.86 to 0.88 represents at least 50% of all compounds other than BL-8040 (SEQ ID NO: 1) in the composition-of-matter (determined as described herein). In some embodiments, the at least one compound characterized by a relative retention time in a range of from 0.86 to 0.88 represents at least 60% of all compounds other than BL-8040 (SEQ ID NO: 1) in the composition-of-matter (determined as described herein). In some embodiments, the at least one compound characterized by a relative retention time in a range of from 0.86 to 0.88 represents at least 70% of all compounds other than BL-8040 (SEQ ID NO: 1) in the composition-of-matter (determined as described herein). In some embodiments, the at least one compound characterized by a relative retention time in a range of from 0.86 to 0.88 represents at least 80% of all compounds other than BL-8040 (SEQ ID NO: 1) in the composition-of-matter (determined as described herein). In some embodiments, the at least one compound characterized by a relative retention time in a range of from 0.86 to 0.88 represents at least 90% of all compounds other than BL-8040 (SEQ ID NO: 1) in the composition-of-matter (determined as described herein).

In some of any of the embodiments described herein, a total concentration ratio (as defined herein) of the at least one compound characterized by a relative retention time in a range of from 0.71 to 0.73 (according to any of the embodiments described herein) to BL-8040 (SEQ ID NO: 1) is at least about 0.01%. In some such embodiments, the total concentration ratio is at least about 0.02%. In some embodiments, the total concentration ratio is at least about 0.03%. In some embodiments, the total concentration ratio is at least about 0.05%. In some embodiments, the total concentration ratio is at least about 0.075%. In some embodiments, the total concentration ratio is at least about 0.1%. In some embodiments, the total concentration ratio is at least about 0.2%. In some embodiments, the total concentration ratio is at least about 0.3%. In some embodiments, the total concentration ratio is at least about 0.4%.

In some of any of the embodiments described herein, a total concentration ratio of the at least one compound characterized by a relative retention time in a range of from 0.71 to 0.73 (according to any of the embodiments described herein) to BL-8040 (SEQ ID NO: 1) is no more than about 0.5%. In some such embodiments, the total concentration ratio is in a range of from 0.01% to 0.5%. In some embodiments, the total concentration ratio is in a range of from 0.02% to 0.5%. In some embodiments, the total concentration ratio is in a range of from 0.03% to 0.5%. In some embodiments, the total concentration ratio is in a range of from 0.05% to 0.5%. In some embodiments, the total concentration ratio is in a range of from 0.075% to 0.5%. In some embodiments, the total concentration ratio is in a range of from 0.1% to 0.5%. In some embodiments, the total concentration ratio is in a range of from 0.2% to 0.5%. In some embodiments, the total concentration ratio is in a range of from 0.3% to 0.5%.

In some of any of the embodiments described herein, a total concentration ratio of the at least one compound characterized by a relative retention time in a range of from 0.71 to 0.73 (according to any of the embodiments described herein) to BL-8040 (SEQ ID NO: 1) is no more than about 0.3%. In some such embodiments, the total concentration ratio is in a range of from 0.01% to 0.3%. In some embodiments, the total concentration ratio is in a range of from 0.02% to 0.3%. In some embodiments, the total concentration ratio is in a range of from 0.03% to 0.3%. In some embodiments, the total concentration ratio is in a range of from 0.05% to 0.3%. In some embodiments, the total concentration ratio is in a range of from 0.075% to 0.3%. In some embodiments, the total concentration ratio is in a range of from 0.1% to 0.3%. In some embodiments, the total concentration ratio is in a range of from 0.2% to 0.3%.

In some of any of the embodiments described herein, a total concentration ratio of the at least one compound characterized by a relative retention time in a range of from 0.71 to 0.73 (according to any of the embodiments described herein) to BL-8040 (SEQ ID NO: 1) is no more than about 0.15%. In some such embodiments, the total concentration ratio is in a range of from 0.01% to 0.15%. In some embodiments, the total concentration ratio is in a range of from 0.02% to 0.15%. In some embodiments, the total concentration ratio is in a range of from 0.03% to 0.15%. In some embodiments, the total concentration ratio is in a range of from 0.05% to 0.15%. In some embodiments, the total concentration ratio is in a range of from 0.075% to 0.15%. In some embodiments, the total concentration ratio is in a range of from 0.1% to 0.15%.

In some of any of the embodiments described herein, the at least one compound characterized by a relative retention time in a range of from 0.71 to 0.73 (according to any of the embodiments described herein) represents at least 10% of all compounds other than BL-8040 (SEQ ID NO: 1) in the composition-of-matter as determined according to absorption at a wavelength at about 226 nm (as defined herein). In some such embodiments, the at least one compound characterized by a relative retention time in a range of from 0.71 to 0.73 represents at least 20% of all compounds other than BL-8040 (SEQ ID NO: 1) in the composition-of-matter (determined as described herein). In some embodiments, the at least one compound characterized by a relative retention time in a range of from 0.71 to 0.73 represents at least 30% of all compounds other than BL-8040 (SEQ ID NO: 1) in the composition-of-matter (determined as described herein). In some embodiments, the at least one compound characterized by a relative retention time in a range of from 0.71 to 0.73 represents at least 40% of all compounds other than BL-8040 (SEQ ID NO: 1) in the composition-of-matter (determined as described herein). In some embodiments, the at least one compound characterized by a relative retention time in a range of from 0.71 to 0.73 represents at least 50% of all compounds other than BL-8040 (SEQ ID NO: 1) in the composition-of-matter (determined as described herein). In some embodiments, the at least one compound characterized by a relative retention time in a range of from 0.71 to 0.73 represents at least 60% of all compounds other than BL-8040 (SEQ ID NO: 1) in the composition-of-matter (determined as described herein). In some embodiments, the at least one compound characterized by a relative retention time in a range of from 0.71 to 0.73 represents at least 70% of all compounds other than BL-8040 (SEQ ID NO: 1) in the composition-of-matter (determined as described herein). In some embodiments, the at least one compound characterized by a relative retention time in a range of from 0.71 to 0.73 represents at least 80% of all compounds other than BL-8040 (SEQ ID NO: 1) in the composition-of-matter (determined as described herein).

In some of any of the embodiments described herein, a total concentration of the at least one compound characterized by a relative retention time in a range of from 0.71 to 0.73 (according to any of the embodiments described herein) and the at least one compound characterized by a relative retention time in a range of from 0.86 to 0.88 (according to any of the embodiments described herein) represents at least 50% of all compounds other than BL-8040 (SEQ ID NO: 1) in the composition-of-matter as determined according to absorption at a wavelength at about 226 nm (as defined herein). In some such embodiments, the total concentration represents at least 60% of all compounds other than BL-8040 (SEQ ID NO: 1) in the composition-of-matter (determined as described herein). In some embodiments, the total concentration represents at least 70% of all compounds other than BL-8040 (SEQ ID NO: 1) in the composition-of-matter (determined as described herein). In some embodiments, the total concentration represents at least 80% of all compounds other than BL-8040 (SEQ ID NO: 1) in the composition-of-matter (determined as described herein). In some embodiments, the total concentration represents at least 90% of all compounds other than BL-8040 (SEQ ID NO: 1) in the composition-of-matter (determined as described herein). In some embodiments, the total concentration represents at least 95% of all compounds other than BL-8040 (SEQ ID NO: 1) in the composition-of-matter (determined as described herein). In some embodiments, the total concentration represents at least 98% of all compounds other than BL-8040 (SEQ ID NO: 1) in the composition-of-matter (determined as described herein). In some embodiments, the total concentration represents at least 99% of all compounds other than BL-8040 (SEQ ID NO: 1) in the composition-of-matter (determined as described herein).

In some of any of the embodiments described herein, the composition-of-matter is characterized by a relatively low amount of deamidated BL-8040 (SEQ ID NO: 2) (wherein the C-terminus is a carboxylic acid rather than an amide) and/or D-Lys(Ac) BL-8040 (SEQ ID NO: 3) (wherein the D-Lys residue is acetylated).

In some of any of the embodiments described herein, a concentration of cyclic deamidated BL-8040 (SEQ ID NO: 2) in the composition-of-matter is no more than 50% of a total concentration of the at least one compound characterized by a relative retention time in a range of from 0.86 to 0.88 according to any of the embodiments described herein. In some such embodiments, the concentration of cyclic deamidated BL-8040 (SEQ ID NO: 2) is no more than 30% of a total concentration of the aforementioned at least one compound characterized by a relative retention time in a range of from 0.86 to 0.88. In some such embodiments, the concentration of cyclic deamidated BL-8040 (SEQ ID NO: 2) is no more than 20% of a total concentration of the aforementioned at least one compound characterized by a relative retention time in a range of from 0.86 to 0.88. In some such embodiments, the concentration of cyclic deamidated BL-8040 (SEQ ID NO: 2) is no more than 10% of a total concentration of the aforementioned at least one compound characterized by a relative retention time in a range of from 0.86 to 0.88. In some such embodiments, the concentration of cyclic deamidated BL-8040 (SEQ ID NO: 2) is no more than 5% of a total concentration of the aforementioned at least one compound characterized by a relative retention time in a range of from 0.86 to 0.88. In some such embodiments, the concentration of cyclic deamidated BL-8040 (SEQ ID NO: 2) is no more than 3% of a total concentration of the aforementioned at least one compound characterized by a relative retention time in a range of from 0.86 to 0.88. In some such embodiments, the concentration of cyclic deamidated BL-8040 (SEQ ID NO: 2) is no more than 2% of a total concentration of the aforementioned at least one compound characterized by a relative retention time in a range of from 0.86 to 0.88. In some such embodiments, the concentration of cyclic deamidated BL-8040 (SEQ ID NO: 2) is no more than 1% of a total concentration of the aforementioned at least one compound characterized by a relative retention time in a range of from 0.86 to 0.88.

In some of any of the embodiments described herein, a concentration of cyclic deamidated BL-8040 (SEQ ID NO: 2) in the composition-of-matter is no more than a total concentration of the at least one compound characterized by a relative retention time in a range of from 0.71 to 0.73 according to any of the embodiments described herein. In some such embodiments, the concentration of cyclic deamidated BL-8040 (SEQ ID NO: 2) is no more than 60% of a total concentration of the aforementioned at least one compound characterized by a relative retention time in a range of from 0.71 to 0.73. In some such embodiments, the concentration of cyclic deamidated BL-8040 (SEQ ID NO: 2) is no more than 40% of a total concentration of the aforementioned at least one compound characterized by a relative retention time in a range of from 0.71 to 0.73. In some such embodiments, the concentration of cyclic deamidated BL-8040 (SEQ ID NO: 2) is no more than 20% of a total concentration of the aforementioned at least one compound characterized by a relative retention time in a range of from 0.71 to 0.73. In some such embodiments, the concentration of cyclic deamidated BL-8040 (SEQ ID NO: 2) is no more than 10% of a total concentration of the aforementioned at least one compound characterized by a relative retention time in a range of from 0.71 to 0.73. In some such embodiments, the concentration of cyclic deamidated BL-8040 (SEQ ID NO: 2) is no more than 5% of a total concentration of the aforementioned at least one compound characterized by a relative retention time in a range of from 0.71 to 0.73. In some such embodiments, the concentration of cyclic deamidated BL-8040 (SEQ ID NO: 2) is no more than 2% of a total concentration of the aforementioned at least one compound characterized by a relative retention time in a range of from 0.71 to 0.73. In some such embodiments, the concentration of cyclic deamidated BL-8040 (SEQ ID NO: 2) is no more than 1% of a total concentration of the aforementioned at least one compound characterized by a relative retention time in a range of from 0.71 to 0.73.

In some of any of the embodiments described herein, a concentration of cyclic D-Lys(Ac) BL-8040 (SEQ ID NO: 3) in the composition-of-matter is no more than 50% of a total concentration of the at least one compound characterized by a relative retention time in a range of from 0.86 to 0.88 according to any of the embodiments described herein. In some such embodiments, the concentration of cyclic D-Lys(Ac) BL-8040 (SEQ ID NO: 3) is no more than 30% of a total concentration of the aforementioned at least one compound characterized by a relative retention time in a range of from 0.86 to 0.88. In some such embodiments, the concentration of cyclic D-Lys(Ac) BL-8040 (SEQ ID NO: 3) is no more than 20% of a total concentration of the aforementioned at least one compound characterized by a relative retention time in a range of from 0.86 to 0.88. In some such embodiments, the concentration of cyclic D-Lys(Ac) BL-8040 (SEQ ID NO: 3) is no more than 10% of a total concentration of the aforementioned at least one compound characterized by a relative retention time in a range of from 0.86 to 0.88. In some such embodiments, the concentration of cyclic D-Lys(Ac) BL-8040 (SEQ ID NO: 3) is no more than 5% of a total concentration of the aforementioned at least one compound characterized by a relative retention time in a range of from 0.86 to 0.88. In some such embodiments, the concentration of cyclic D-Lys(Ac) BL-8040 (SEQ ID NO: 3) is no more than 3% of a total concentration of the aforementioned at least one compound characterized by a relative retention time in a range of from 0.86 to 0.88. In some such embodiments, the concentration of cyclic D-Lys(Ac) BL-8040 (SEQ ID NO: 3) is no more than 2% of a total concentration of the aforementioned at least one compound characterized by a relative retention time in a range of from 0.86 to 0.88. In some such embodiments, the concentration of cyclic D-Lys(Ac) BL-8040 (SEQ ID NO: 3) is no more than 1% of a total concentration of the aforementioned at least one compound characterized by a relative retention time in a range of from 0.86 to 0.88.

In some of any of the embodiments described herein, a concentration of cyclic D-Lys(Ac) BL-8040 (SEQ ID NO: 3) in the composition-of-matter is no more than a total concentration of the at least one compound characterized by a relative retention time in a range of from 0.71 to 0.73 according to any of the embodiments described herein. In some such embodiments, the concentration of cyclic D-Lys(Ac) BL-8040 (SEQ ID NO: 3) is no more than 60% of a total concentration of the aforementioned at least one compound characterized by a relative retention time in a range of from 0.71 to 0.73. In some such embodiments, the concentration of cyclic D-Lys(Ac) BL-8040 (SEQ ID NO: 3) is no more than 40% of a total concentration of the aforementioned at least one compound characterized by a relative retention time in a range of from 0.71 to 0.73. In some such embodiments, the concentration of cyclic D-Lys (Ac) BL-8040 (SEQ ID NO: 3) is no more than 20% of a total concentration of the aforementioned at least one compound characterized by a relative retention time in a range of from 0.71 to 0.73. In some such embodiments, the concentration of cyclic D-Lys(Ac) BL-8040 (SEQ ID NO: 3) is no more than 10% of a total concentration of the aforementioned at least one compound characterized by a relative retention time in a range of from 0.71 to 0.73. In some such embodiments, the concentration of cyclic D-Lys (Ac) BL-8040 (SEQ ID NO: 3) is no more than 5% of a total concentration of the aforementioned at least one compound characterized by a relative retention time in a range of from 0.71 to 0.73. In some such embodiments, the concentration of cyclic D-Lys(Ac) BL-8040 (SEQ ID NO: 3) is no more than 2% of a total concentration of the aforementioned at least one compound characterized by a relative retention time in a range of from 0.71 to 0.73. In some such embodiments, the concentration of cyclic D-Lys(Ac) BL-8040 (SEQ ID NO: 3) is no more than 1% of a total concentration of the aforementioned at least one compound characterized by a relative retention time in a range of from 0.71 to 0.73.

In some of any of the embodiments described herein, a total concentration of cyclic deamidated BL-8040 (SEQ ID NO: 2) and cyclic D-Lys(Ac) BL-8040 (SEQ ID NO: 3) in the composition-of-matter is no more than 80% of a total concentration of the at least one compound characterized by a relative retention time in a range of from 0.86 to 0.88 according to any of the embodiments described herein. In some such embodiments, the total concentration of cyclic deamidated BL-8040 (SEQ ID NO: 2) and cyclic D-Lys(Ac) BL-8040 (SEQ ID NO: 3) is no more than 60% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 50% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 40% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 30% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 20% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 10% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 5% of a total concentration of the aforementioned at least one compound characterized by a relative retention time in a range of from 0.86 to 0.88. In some such embodiments, the total concentration of cyclic deamidated BL-8040 (SEQ ID NO: 2) and cyclic D-Lys(Ac) BL-8040 (SEQ ID NO: 3) is no more than 2% of a total concentration of the aforementioned at least one compound characterized by a relative retention time in a range of from 0.86 to 0.88.

In some of any of the embodiments described herein, a total concentration of cyclic deamidated BL-8040 (SEQ ID NO: 2) and cyclic D-Lys(Ac) BL-8040 (SEQ ID NO: 3) in the composition-of-matter is no more than 150% of a total concentration of the at least one compound characterized by a relative retention time in a range of from 0.71 to 0.73 according to any of the embodiments described herein. In some such embodiments, the total concentration of cyclic deamidated BL-8040 (SEQ ID NO: 2) and cyclic D-Lys(Ac) BL-8040 (SEQ ID NO: 3) is no more than 120% of a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than 80% of a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than 60% of a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than 40% of a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than 20% of a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than 10% of a total concentration of the aforementioned at least one compound characterized by a relative retention time in a range of from 0.71 to 0.73. In some such embodiments, the total concentration of cyclic deamidated BL-8040 (SEQ ID NO: 2) and cyclic D-Lys(Ac) BL-8040 (SEQ ID NO: 3) is no more than 5% of a total concentration of the aforementioned at least one compound characterized by a relative retention time in a range of from 0.71 to 0.73.

Without being bound by any particular theory, it is believed that the cyclic forms of SEQ ID NO: 2 and/or SEQ ID NO: 3 are not necessarily more deleterious than the corresponding non-cyclic forms, but rather the non-cyclic forms will typically be considerably rarer (e.g., under conditions in which the peptide having SEQ ID NO: 1 is predominantly in cyclic form), and thus may optionally be disregarded for convenience.

The above mentioned peptides—cyclic deamidated BL-8040 (SEQ ID NO: 2) and/or cyclic D-Lys(Ac) BL-8040 (SEQ ID NO: 3)—may optionally be quantified by determining retention times under conditions described herein, e.g., using a reference sample of the peptide to precisely identify the relative retention time (relative to the retention time of BL-8040 (SEQ ID NO: 1), as defined herein). For example, under the HPLC conditions described herein, the relative retention time of cyclic deamidated BL-8040 (SEQ ID NO: 2) is typically about 0.91, and the relative retention time of cyclic D-Lys(Ac) BL-8040 (SEQ ID NO: 3) is about 1.10.

Process:

As exemplified herein, compositions-of-matter such as described herein may optionally be prepared using solid phase synthesis, in which the peptide (in a protected form) is formed attached to a resin and then cleaved from the resin (while removing protecting groups). Intramolecular disulfide bonds, to form the cyclic peptide, may then be formed by oxidation of Cys residues.

In some of any of the embodiments described herein, the process is a large-scale process.

Herein, the term "large-scale process" refers to a process for preparation of at least 100 grams (in a single run of the process) of the final product (BL-8040 (SEQ ID NO: 1)).

In some of any of the embodiments described herein relating to a large-scale process, at least 250 grams of BL-8040 (SEQ ID NO: 1) peptide are prepared, or at least 500 grams of the cyclic peptide, or at least 1 kg of the cyclic peptide, or at least 3 kg of the cyclic peptide, or even at least 10 kg of cyclic peptide are prepared by the process.

According to some embodiments of the present invention, compositions-of-matter as described herein are obtainable by a process as described herein.

In some of any of the embodiments described herein relating to a process, the obtained composition-of-matter according to any of the respective embodiments described is associated with a characteristic set of minor components other than BL-8040 (SEQ ID NO: 1), e.g., representing a "signaturion" of the process.

The sum of all compounds other than BL-8040 (SEQ ID NO: 1), as defined according to any of the respective embodiments described herein, is also referred to herein interchangeably as a "signatory composition", which characterizes the process as described herein.

Without being bound by any particular theory, it is believed that the signatory composition is associated with enhanced biological activity described herein (e.g., in the section relating to biological activity).

According to some embodiments of the present invention, the process as described herein provides a signatory composition-of-matter (a signaturion, as described herein), which comprises BL-8040 (SEQ ID NO: 1) and an advantageous signatory composition of compounds other than BL-8040 (SEQ ID NO: 1), as described herein in any of the respective embodiments.

As detailed herein, the process preferably comprises sequentially coupling amino acids and 4-fluoro-benzoic acid to a resin (e.g., Rink AMS resin) by solid phase peptide synthesis (according to general procedures known in the art), to obtain a linear peptide coupled to the resin. The order of the sequential coupling is Arg, Cys, Cit (citrulline), Arg, Tyr, Pro, DLys (D-lysine), Lys, Cit, Tyr, Cys, Nal (naphthylalanine), Arg, Arg, 4-fluoro-benzoic acid.

The process further comprises cleaving the peptide formed by coupling from the resin, thereby obtaining a free peptide having SEQ ID NO: 1 in non-cyclic form, and oxidizing the cysteine residues therein to form an intramolecular disulfide bond, thereby obtaining the cyclic form (in solution).

Coupling comprises forming an amide bond between a carboxylate group (e.g., of an amino acid or N-terminal carboxylic acid) and an amine group (e.g., of a resin in the first step or an N-terminus in subsequent steps), and is preferably effected using one or more coupling reagents known in the art to be suitable for amide bond formation, for example, a carbodiimide (e.g., 1-ethyl-3-(3-dimethylaminopropyl)carbodiimide, dicyclohexylcarbodiimide and/or diisopropylcarbodiimide), aminium/uronium (e.g., HATU, HBTU, TBTU and/or HCTU) or phosphonium salt (e.g., PyBOP and/or PyAOP) and/or propanephosphonic acid anhydride.

The one or more coupling reagents optionally comprises a carbodiimide (e.g., diisopropylcarbodiimide) and an additional agent (e.g., in about the same molar concentration as the carbodiimide) such as a hydroxytriazole (e.g., 1-hydroxy-benzotriazole (HOBt) or 1-hydroxy-7-azabenzotriazole (HOAt) and/or a cyanohydroxyiminoacetate ester (e.g., ethyl cyanohydroxyiminoacetate).

Coupling may optionally be effected using a carbodiimide and a cyanohydroxyiminoacetate ester, for example, wherein the carbodiimide and/or the cyanohydroxyiminoacetate ester are used in a molar excess of about two-fold (relative to the amino acid or other carboxylic acid being coupled).

Coupling may optionally be effected using a carbodiimide with ethyl cyanohydroxyiminoacetate and/or N-hydroxybenzotriazole, for example, wherein the carbodiimide and/or the ethyl cyanohydroxyiminoacetate and/or N-hydroxybenzotriazole are used in a molar excess of about two-fold (relative to the amino acid or other carboxylic acid being coupled).

Coupling may optionally be effected using diisopropylcarbodiimide (DIC) with ethyl cyanohydroxyiminoacetate and/or N-hydroxybenzotriazole, for example, wherein the DIC and the ethyl cyanohydroxyiminoacetate and/or N-hydroxybenzotriazole are used in a molar excess of about two-fold (relative to the amino acid or other carboxylic acid being coupled).

At each amino acid coupling step, the N-terminus of the amino acid is protected by a readily removable group, preferably fluorenylmethyloxycarbonyl (Fmoc), which may optionally be cleaved by a mild base such as piperidine (e.g., 20-50% piperidine in DMF). An exemplary concentration of piperidine in DMF is about 20%.

For example, Fmoc groups may optionally be removed by washing twice in piperidine solution (according to any of the embodiments described herein), optionally once for 5-10 minutes and then optionally once for 25-30 minutes; followed by washing of the resin (e.g., in DMF without piperidine) to remove the base (which may optionally be ascertained by determining pH).

In addition, side chains of certain amino acids may be protected by a readily removable group (which is not cleaved by the abovementioned mild base), such as t-butoxy. Thus, side chain hydroxy groups in Tyr may preferably be protected by t-butyl (t-Bu) (to form a t-butoxy group), and side chain amine groups in (L or D) Lys may be protected by t-butoxycarbonyl (Boc) (which comprises a t-butoxy group); and in both cases, cleavage (e.g., in an acidic environment) may regenerate the unprotected hydroxy or amine group. Similarly, side chain thiohydroxy groups of Cys may preferably be protected with trityl (Trt), and/or side chain guanidinium groups of Arg may preferably be protected with 2,2,4,6,7-pentamethyl-2,3-dihydrobenzofuran-5-sulfonyl (Pbf); each of which may optionally be cleaved in an acidic environment. The aforementioned side chain protective groups are known for being particularly compatible with the use of Fmoc. The skilled person will be aware of additional protective groups suitable for specific groups in amino acid side chains, and their compatibility with each other and with various N-terminal protective groups.

The resin to which the amino acids are sequentially coupled is optionally a Rink aminomethylstyrene (AMS) resin (aminomethylstyrene resin substituted with a Rink linker). The Rink AMS resin is optionally protected by Fmoc groups, which may be removed prior to coupling so as to expose amine groups (to which the first amino acid is coupled).

The degree of substitution of the resin (optionally a Rink AMS resin) to which the amino acids are sequentially coupled is optionally at least 0.3 milliequivalents per gram resin (e.g., from 0.3 to 0.11 milliequivalents per gram resin), optionally at least 0.6 milliequivalents per gram resin, optionally from 0.6 to 1.1 milliequivalents per gram resin, and optionally from 0.6 to 0.9 milliequivalents per gram resin.

The resin is optionally washed (e.g., once or twice) with a solvent such as dimethylformamide (DMF) prior to each coupling step, for example, to facilitate swelling of the resin. In some exemplary embodiments, the resin is washed for 20-30 minutes prior to de-protection of the resin (e.g., removal of Fmoc groups according to any of the respective embodiments described herein) and coupling of the first amino acid, and washed (e.g., twice) for about 2 minutes prior to each subsequent coupling step.

Cleavage of the peptide (formed by sequential coupling) from the resin, and cleavage of the protecting groups from the amino acid side chains, is preferably effected by contacting the peptide (coupled to the resin) with a liquid comprising an acid such as trifluoroacetic acid (TFA). The concentration of TFA in the liquid is optionally at least about 80%, or at least about 90%, or at least about 95% by weight (e.g., wherein the balance is primarily water).

The liquid (e.g., acidic liquid) used for cleavage optionally further comprises a scavenger (e.g., a scavenger of reactive cationic species which may form during cleavage), such as thiols (e.g., ethanedithiol, dithioerythritol, dithiothreitol), trialkylsilanes, (e.g., triisopropylsilane), phenols (e.g., m-cresol) and/or water.

Dithiothreitol (DTT) and/or dithioerythritol (DTE) are examples of a suitable scavenger, optionally wherein the liquid is a solution comprising TFA (e.g., at a concentration described herein) and DTT and/or DTE, preferably in combination with water. The (total) concentration of DTT and/or DTE in a solution used for cleavage is optionally at least 10 mg/mL (e.g., from 10 to 500 mg/mL, or from 10 to 200 mg/mL, or from 10 to 100 mg/mL, or from 10 to 50 mg/mL), optionally at least 25 mg/mL (e.g., from 25 to 500 mg/mL, or from 25 to 200 mg/mL, or from 25 to 100 mg/mL, or from 25 to 50 mg/mL), optionally at least 50 mg/mL (e.g., from 50 to 500 mg/mL, or from 50 to 200 mg/mL, or from 50 to 100 mg/mL), and optionally about 50 mg/mL.

Upon cleavage of the peptide from the resin, the free peptide is preferably precipitated, for example, by addition of a liquid in which the peptide is insoluble. Precipitation is optionally preceded by concentrating the free peptide by evaporation of a portion of solvent of the solution, thus reducing a volume of the solution (e.g., by about 65% to about 70%). Alternatively, no concentration of free peptide is performed prior to precipitation.

In some of any of the embodiments described herein, precipitation of the free peptide is performed without concentrating the free peptide prior to precipitation.

Precipitation of the peptide is optionally effected by addition of a dialkyl ether, such as tert-butyl methyl ether (MTBE).

The MTBE is optionally admixed with hexane. In some embodiments, the mixture of MTBE and hexane (optionally chilled, e.g., to a temperature in a range of about 5° C. to about 15° C.) is added to the peptide at a volume of at least 40 mL mixture per gram of resin, and optionally about 45 mL mixture per gram of resin. Exemplary mixtures of MTBE and hexane are composed of MTBE and hexane at a 60:40 (MTBE: hexane) volume ratio.

The precipitated peptide is optionally dried, for example, by lyophilization or by vacuum.

As discussed herein, an intramolecular disulfide bond may be formed (resulting in cyclization of the peptide) by oxidizing cysteine residues of the obtained peptide. Any suitable technique known in the art may optionally be used.

Such oxidizing is optionally effected by contacting the peptide with hydrogen peroxide, for example, by gradual (e.g., dropwise) addition of a hydrogen peroxide solution (e.g., about 1.5% by weight hydrogen peroxide in water). The molar ratio of hydrogen peroxide to pair of Cys residues (e.g., to peptide, wherein the peptide comprises exactly two Cys residues, such as in SEQ ID NO: 1) is preferably at least 1:1 (i.e., there is at least one hydrogen peroxide molecule per pair of Cys residues), optionally at least 2:1, optionally at least 3:1, and optionally at least 4:1. An exemplary molar ratio of hydrogen peroxide to pair of Cys residues (e.g., to peptide) is at about 5:1. Alternatively or additionally, hydrogen peroxide may optionally be added until no thiohydroxy groups remain (e.g., as determined by a suitable assay, such as an Ellman test).

Oxidizing is optionally effected by contacting an aqueous solution comprising the peptide at a concentration of at least 5 mg/mL (e.g., from 5 to 20 mg/mL, or from 5 to 15 mg/mL, or from 5 to 10 mg/mL, or about 10 mg/mL) with hydrogen peroxide (e.g., according to any of the respective embodiments described herein). Optionally the peptide concentration is at least 10 mg/mL (e.g., from 10 to 20 mg/mL, or from 10 to 15 mg/mL). The aqueous solution is optionally mildly alkaline, for example, an aqueous solution of ammonium bicarbonate ($NH_4HCO_3$). An exemplary concentration of ammonium bicarbonate is about 0.1 M.

The process preferably further comprises isolating the obtained BL-8040 (SEQ ID NO: 1). As the isolation procedure will not be 100% perfect, some additional compounds (as described herein) remain. Any suitable technique known in the art may optionally be used.

Isolation of the peptide optionally comprises chromatography, for example, at least one step (e.g., optionally one or two steps) of preparative high performance liquid chromatography (HPLC), for example, using a C18 column. Isolation optionally comprises loading the obtained peptide (e.g., in at least one step of HPLC described herein) on a reverse phase chromatography column (e.g., a C18 column) at a concentration of no more than 40 grams peptide per kg of the column (by weight of resin of the column); and/or optionally at a concentration of at least 4 grams (e.g., from 4 to 40 grams or from 4 to 30 grams or from 4 to 25 grams) peptide per kg of the column (by weight of resin of the column), optionally of at least 10 grams (e.g., from 10 to 40 grams or from 10 to 30 grams or from 10 to 25 grams) peptide per kg of the column, and optionally of at least 20 grams (e.g., from 20 to 40 grams or from 20 to 30 grams or from 20 to 25 grams) peptide per kg of the column.

The peptide loaded on a column (according to any of the respective embodiments described herein) is eluted, e.g., using a buffer solution (e.g., in combination with an acetonitrile gradient, according to any of the respective embodiments described herein). The pH of the buffer solution is optionally in a range of from 1.5 to 3, optionally from 2.0 to 2.5, and optionally about 2.25. Triethylammonium phosphate buffer may optionally be used to elute the peptide from the column, for example, at a concentration of at least about 0.01 M, or at least about 0.03 M, or at least about 0.1 M. In exemplary embodiments, the concentration of triethylammonium phosphate is about 0.1 M.

Elution from an HPLC column is optionally effected with an acetonitrile gradient. The gradient optionally comprises increasing a concentration of acetonitrile by a rate (which is optionally varied over time) in a range of from 0.1% acetonitrile per minute to 2% acetonitrile per minute, e.g., about 1% per 5-6 minutes and/or about 1% per minute. Alternatively or additionally, the gradient optionally comprises increasing a concentration of acetonitrile (e.g., from 0%) to a concentration in a range of from 10% to 40%, or from 20% to 30%, or to about 25%.

An exemplary gradient (e.g., using triethylammonium phosphate buffer according to any of the respective embodiments described herein) comprises 0% acetonitrile for about 8 minutes, from 0% to about 5% acetonitrile in about 5 minutes (e.g., a rate of about 1% per minute), and from about 5% to about 25% acetonitrile in about 120 minutes (e.g., a rate of about 0.17% per minute).

Optionally, eluted peptide is loaded on a column (according to any of the respective embodiments described herein) a second time and eluted, e.g., using a buffer solution (e.g., in combination with an acetonitrile gradient, according to any of the respective embodiments described herein). Acetic acid buffer (e.g., acetic acid/ammonium acetate) may optionally be used to elute the peptide from the column (e.g., in order to obtain the peptide as an acetate salt), for example, at a concentration of at least about 5 mM, or at least about 20 mM, or at least about 35 mM. In exemplary embodiments, the concentration of acetate is about 35 mM.

An exemplary gradient (e.g., using acetic acid buffer according to any of the respective embodiments described herein) for a second elution comprises 0% acetonitrile for 8 minutes, and from 0% to 22% acetonitrile in 110 minutes (a rate of 0.2% per minute).

The process optionally further comprises lyophilizing the product obtained by chromatography (e.g., according to any of the respective embodiments described herein).

Optionally, the process is characterized by at least one, or at least two, or at least three, or at least four, or at least five, or at least six of the following features (i)-(vii):
(i) coupling is effected using diisopropylcarbodiimide (DIC) in combination with ethyl cyanohydroxyiminoacetate and/or N-hydroxybenzotriazole (e.g., according to any of the respective embodiments described herein);
(ii) cleavage of the peptide from the resin is effected by contacting the linear peptide coupled to the resin with a solution comprising trifluoroacetic acid (TFA) and a scavenger which is dithiothreitol (DTT) and/or dithioerythritol (DTE) (e.g., according to any of the respective embodiments described herein);
(iii) the process further comprises precipitating the free linear peptide after cleaving without concentrating the free linear peptide by evaporation prior to precipitation of the peptide (e.g., according to any of the respective embodiments described herein);
(iv) oxidation comprises contacting an aqueous solution comprising the linear peptide at a concentration of at least 5 mg/mL with hydrogen peroxide (e.g., according to any of the respective embodiments described herein);
(v) isolating the peptide comprises loading the cyclic peptide on a reverse phase chromatography column at a concentration of no more than 40 grams cyclic peptide per kg of the column, and eluting the cyclic peptide from the column (e.g., according to any of the respective embodiments described herein);
(vi) isolating the cyclic peptide comprises lyophilization, and the process further comprises grinding the cyclic peptide following lyophilization (e.g., according to any of the respective embodiments described herein); and/or
(vii) a degree of substitution of the resin used for peptide synthesis is at least 0.3 milliequivalents per gram and/or the resin is a Rink AMS resin (e.g., according to any of the respective embodiments described herein).

Biological Activity:

In some of any of the respective embodiments, a BL-8040 (SEQ ID NO: 1)-containing composition-of-matter according to any of the respective embodiments described herein exhibits an enhanced biological activity as compared to a corresponding BL-8040 (SEQ ID NO: 1)-containing composition-of-matter (e.g., with the same BL-8040 (SEQ ID NO: 1) concentration, counter-ions and solvent) without a compound having a relative retention rate of 0.71 to 0.73 and/or 0.86 to 0.88 (according to any of the respective embodiments described herein).

In some of any of the respective embodiments, the biological activity of the composition-of-matter is characterized by promotion of in vivo neutrophil migration to peripheral blood (which may also be regarded as inhibition of migration to bone marrow), e.g., in mice.

As exemplified herein, a composition-of-matter according to embodiments of the invention (e.g., with a signatory composition comprising compounds having relative retention times of about 0.72 and about 0.87) was associated with an almost two-fold enhancement of the increase in neutrophils in peripheral blood, relative to a control composition-of-matter comprising the same amount of BL-8040 (SEQ ID NO: 1) without the aforementioned additional compounds.

In some of any of the respective embodiments, promotion of in vivo neutrophil migration to peripheral blood is determined by subcutaneously injecting mice with 5 mg/kg of BL-8040 (SEQ ID NO: 1), reconstituted in 200 µl of PBS, then bleeding the mice 2 hours after injection (e.g., by cardiac puncture into tubes with heparin) and quantifying the number of mature neutrophils in the peripheral blood (e.g., by flow cytometry) relative to control (untreated) mice.

In some of any of the respective embodiments, the biological activity of the composition-of-matter is characterized by one or more of the following:
(i) promotion of in vivo neutrophil migration to peripheral blood (which may also be regarded as inhibition of migration to bone marrow), e.g., in mice;
(ii) inhibition of in vitro CXCL12-induced migration of breast cancer cells;
(iii) inhibition of in vitro CXCL12-induced migration of T-cell-derived leukemia cells;
(iv) inhibition of metastatic breast cancer cell migration to lungs in an animal (e.g., mouse) model;
(v) inhibition of delayed-type hypersensitivity in an animal (e.g., mouse) model;
(vi) inhibition of collagen-induced arthritis in an animal (e.g., mouse) model; and
(vii) inhibition of binding of CXCL12 to CXCR4 in cells (e.g., Jurkat cells) in vitro (e.g., increasing an $IC_{50}$ of the CXCL12).

In some of the respective embodiments, the biological activity of the composition-of-matter is characterized by at least two of activities (i)-(vii). In some embodiments, the biological activity of the composition-of-matter is characterized by at least three of activities (i)-(vii).

An enhanced biological activity according to any of the respective embodiments described herein is optionally characterized by an increase or decrease in a relevant quantitative parameter (e.g., a fold-change in the parameter relative to control) of at least 10%, optionally at least 20%, optionally at least 30%, and optionally at least 50% (e.g., as determined according to procedures described herein). For example, an enhanced promotion of in vivo neutrophil migration to peripheral blood according to any of the respective embodiments described herein is optionally characterized by an increase in neutrophil levels in the peripheral blood of at least 10%, optionally at least 20%, optionally at least 30%, and optionally at least 50% (e.g., as determined according to procedures described herein).

Activities (i)-(vii) may optionally be evaluated using procedures such as described in U.S. Pat. No. 7,423,007 and/or as described in the Examples section herein.

In some of any of the respective embodiments, activities (ii) and (iii) (inhibition of in vitro CXCL12-induced migration) is determined by evaluating migration of cells through a suitable microporous membrane and/or insert separating two compartments (e.g., of a Transwell® plate). CXCL12 (100 nM for breast cancer cells and 30 nM for leukemia cells) and cell growth medium (optionally 600 µl of DMEM with 0.1% bovine serum albumin) with the BL-8040 (SEQ ID NO: 1) composition is added to a first (e.g., upper) compartment, and the tested BL-8040 (SEQ ID NO: 1) composition and MDA-MB-231 breast cancer cells or SUP-T1 leukemia cells (e.g., at $2 \times 10^6$ cells/ml) and cell growth medium (optionally 100 µl of DMEM with 0.1% bovine serum albumin) are added to the second (e.g., lower) compartment. The amount of cells which migrated through the membrane and/or insert upon incubation (e.g., for 15 hours for breast cancer cells and 4 hours for leukemia cells) under conditions suitable for cell growth and activity (e.g., at 37°

C.) are quantified, optionally by flow cytometry and/or by fixing and staining (e.g., with 25% methanol and 0.5% crystal violet), and compared to a control sample with no BL-8040 (SEQ ID NO: 1).

In some of any of the respective embodiments, activity (iv) (inhibition of metastatic breast cancer cell migration to lungs) is determined by implanting intravenously $10^6$ MDA-MB-231 human breast cancer cells into the tails of mice (optionally five week-old female CB-17 SCID mice). A BL-8040 (SEQ ID NO: 1) composition comprising physiological saline, adjusted to a BL-8040 (SEQ ID NO: 1) concentration of 80 mg/ml is administered gradually over the course of four weeks to the mice (optionally using sustained-release osmotic pumps) to administer about 18.2 mg/kg/day). The amount of cancer cells in the lungs of the mice is then evaluated, optionally using Evan's Blue solution (e.g., 0.2%, 2 ml) injected through the windpipes followed by soaking the lungs in Bouin's liquid, staining and fixing.

In some of any of the respective embodiments, activity (v) (inhibition of delayed-type hypersensitivity) is determined according to the degree of inflammation (represented by change in ankle thickness) generated by injection of sheep red blood cells into ankles of sensitized mice. To sensitize the mice, sheep red blood cells suspended in physiological saline solution ($2\times10^7$ cells per 50 µl) are administered subcutaneously to the ankles of the left hind limbs of mice (optionally 6 week-old male BALB/c mice), and after 5 days, $10^8$ cells per 50 µl sheep red blood cells are administered subcutaneously to the ankles of the right hind limbs. Immediately prior to and about 24 hours after the induction of antigens, the ankle thickness is determined. A BL-8040 (SEQ ID NO: 1) composition comprising PBS is administered gradually to the mice (optionally using sustained-release osmotic pumps) to administer about 4, about 8, about 24 and/or about 120 µg/day BL-8040 (SEQ ID NO: 1), beginning on the day before sensitization.

In some of any of the respective embodiments, activity (vi) (inhibition of collagen-induced arthritis) is determined by generating collagen-induced arthritis in mice (optionally 6 week-old male DBA/1JN mice) via intradermal injection (e.g., into the base of the tail) of an emulsion comprising 1 mg/ml bovine type II collagen, 0.025 M acetic acid, and 50% (by volume) Freund's complete adjuvant, followed by a similar immunization 21 days after the injection. For two weeks after the second immunization, body weight and/or hind limb thickness is optionally measured and arthritis scoring is optionally performed. Arthritis is optionally scored at 0-3 points of each limb, and evaluated by the total of the same (12 points being the full points; 0=normal; 1=mild swelling or swelling of a single digit; 2=moderate swelling or swelling of plural digits; 3=severe swelling). Type II collagen-specific IgG2a antibodies are optionally quantified (at the end of the two week period) using any suitable technique, optionally by the procedures described in the examples section herein. Inhibition of collagen-induced arthritis may optionally be manifested as inhibition of body weight loss, reduction in arthritis score and/or reduction in Type II collagen-specific antibodies.

In some of any of the respective embodiments, activity (vii) (inhibition of binding of CXCL12 to CXCR4 in cells) is optionally determined using radioactively labeled CXCL12 in Jurkat human T-cell leukemia cells (e.g., increasing an $IC_{50}$ of the CXCL12). 200 pM of $^{125}$I-CXCL12 is incubated with Jurkat cells (optionally at $6\times10^6$ cells/ml) suspended in buffer at a pH of about 7 (e.g., Dulbecco's PBS solution, pH 7.0, containing 0.5% bovine serum albumin and 20 mM HEPES) and the tested BL-8040 (SEQ ID NO: 1) composition-of-matter diluted by buffer, at a volume ratio of 1:2:1 (e.g., 25 µl radio-labeled $^{125}$I-CXCL12, 50 µl Jurkat cell solution, and 25 µl BL-8040 (SEQ ID NO: 1) composition in buffer). The samples are subjected to fixation reaction for 1 hour at room temperature, followed by determining each sample's radioactivity.

Formulation and Uses:

The composition-of-matter comprising BL-8040 (SEQ ID NO: 1) (and compounds other than BL-8040 (SEQ ID NO: 1)) according to any of the respective embodiments described herein may optionally be for use in treatment of a condition treatable by BL-8040 (SEQ ID NO: 1).

According to an aspect of some embodiments of the invention, there is provided a use of a composition-of-matter according to any of the respective embodiments described herein in the manufacture of a medicament for treating a condition treatable by BL-8040 (SEQ ID NO: 1).

According to an aspect of some embodiments of the invention, there is provided a method of treating a condition treatable by BL-8040 (SEQ ID NO: 1), the method comprising administering a composition-of-matter according to any of the respective embodiments described herein to a subject in need thereof.

In some of any of the embodiments described herein relating to treatment, the treatment may be any treatment in which inhibiting CXCR4 is advantageous.

It is expected that during the life of a patent maturing from this application many relevant treatments will be developed and the scope of the terms "condition", "treatable by BL-8040" and "treatment in which inhibiting CXCR4 is advantageous" is intended to include all such new technologies a priori.

In some of any of the embodiments described herein, the condition treatable by BL-8040 (SEQ ID NO: 1) is a cancer or arthritis (e.g., chronic rheumatoid arthritis), e.g., as described in U.S. Pat. No. 7,423,007 (the contents of which are incorporated herein by reference, particularly contents regarding treatment of conditions by the aforementioned peptide).

Examples of conditions treatable (according to any of the aspects described herein) by BL-8040 (SEQ ID NO: 1) include, without limitation, retinoblastoma and/or neuroectodermal derived tumors, e.g., as described in International Patent Application Publication WO 2012/095849 (the contents of which are incorporated herein by reference, particularly contents regarding treatment of conditions by the aforementioned peptide); large cell lung cancer, e.g., as described in WO 2013/160895 (the contents of which are incorporated herein by reference, particularly contents regarding treatment of conditions by the aforementioned peptide); multiple myeloma, microglioma and/or glioma, e.g., as described in International Patent Application Publication WO 2008/075370 (the contents of which are incorporated herein by reference, particularly contents regarding treatment of conditions by the aforementioned peptide); breast cancer and/or pancreatic cancer, e.g., as described in U.S. Pat. No. 7,423,007; thrombocytopenia, e.g., as described in International Patent Application Publication WO 2010/146578 (the contents of which are incorporated herein by reference, particularly contents regarding treatment of conditions by the aforementioned peptide); risk of bone marrow suppression, e.g., as described in International Patent Application Publication WO 2008/075369 (the contents of which are incorporated herein by reference, particularly contents regarding treatment of conditions by the aforementioned peptide); and HIV infection, e.g., as described in U.S. Pat. No. 8,435,939 (the contents of which are incorporated herein by reference, particularly contents regarding treatment of conditions by the aforementioned peptide).

Suitable analogs and derivatives of BL-8040 (SEQ ID NO: 1) are described in U.S. Pat. Nos. 7,423,007 and 8,435,939 and International Patent Application Publications WO 2008/075369, WO 2008/075370, WO 2010/146578, WO 2012/095849 and WO 2013/160895 (the contents of each of which are incorporated herein by reference, particularly contents regarding analogs and derivatives of SEQ ID NO: 1).

A composition-of-matter comprising BL-8040 (SEQ ID NO: 1) and compounds other than BL-8040 (SEQ ID NO: 1) according to any of the embodiments described herein can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to BL-8040 (SEQ ID NO: 1), and may further include any additional therapeutically active agent which is optionally formulated with the BL-8040 (SEQ ID NO: 1).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredient(s) into preparations which, can be used pharmaceutically. Proper formulation is dependent upon the route of administration chosen.

For injection, the active ingredient(s) of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active ingredient(s) with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active ingredient(s) in admixture with filler such as lactose, binders such as starches, lubricants such as talc or magnesium stearate and, optionally, stabilizers. In soft capsules, the active ingredient(s) may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, compositions comprising the active ingredient(s) for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredient(s) may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredient(s) to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredient is contained in an amount effective to achieve the intended purpose. More specifically, a therapeutically effective amount of BL-8040 (SEQ ID NO: 1) peptide means an amount of the peptide effective to prevent, alleviate or ameliorate symptoms of a disorder (e.g., a cancer or arthritis, as discussed herein) or prolong the survival of the subject being treated.

Determination of a therapeutically effective amount is well within the capability of those skilled in the art, especially in light of the detailed disclosure provided herein. The exact formulation, route of administration and dosage can be chosen by the individual physician in view of the patient's condition. (See, e.g., Fingl, et al., 1975, in "The Pharmacological Basis of Therapeutics", Ch. 1 p.1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Additional Definitions:

As used herein the term "about" refers to ±10%. In some of any of the respective embodiments described herein, the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Large Scale Phase Synthesis of BL-8040 According to Some Embodiments

The cyclic peptide BL-8040 (SEQ ID NO: 1) was prepared by large scale (825 mmol) solid phase synthesis, wherein solid phase synthesis reaction steps were repeated 14 times for the construction of the entire peptide, beginning with the C-terminal amino acid and ending with the N-terminal amino acid. Each amino acid addition was performed in two steps: the first step includes the removal of the Fmoc protective group from the N-terminus of the last amino acid added to the peptide sequence (or from the resin, when adding the first amino acid), followed by attachment of the sequential amino acid to the elongating of the peptide on the resin. The last residue to be added to the peptide on the resin was the 4-fluorobenzoyl group, which does not contain an Fmoc group.

The final yield was 468 grams (25%)

Resin:
The resin was Fmoc-Rink AMS resin with substitution in a range of 0.3 to 0.6 milliequivalents/gram.
Removal of Fmoc Protective Group:
The Fmoc protective group was removed from the N-terminus (of the last amino acid added to the peptide sequence) or resin using a solution of 20% piperidine in dimethylformamide (DMF) (10 ml per gram of initial resin). Washing with DMF removed the piperidine solution prior to the next amino acid reaction, confirmed by testing pH of the wash.
Attachment of Amino Acid:
The amino acids were coupled in the form of an appropriate amino acid derivative, using diisopropylcarbodiimide (DIC) in combination with HOBt (N-hydroxybenzotriazole) as the activating agent. Cys, Arg, Tyr and Lys (D-Lys or L-Lys) were protected as Cys(Trt), Arg(Pbf), Tyr(t-Bu) and Lys(Boc) (D- or L-), respectively. In the final step, 4-fluorobenzoic acid was coupled instead of an amino acid. Calculations of amino acid (or 4-fluorobenzoic acid), DIC and HOBt quantities were based on a two-fold excess of the substitution and batch size.

In-process monitoring, using the ninhydrin and chloranil tests was performed at the end of each cycle for evaluation of the coupling step. A negative test result indicates the absence of free amino groups (complete coupling). If the test is positive, indicating unreacted amino groups (incomplete coupling), the coupling reaction may be prolonged, or re-coupling of the protected amino acid derivative may be performed.

After the synthetic cycles were complete, the resin-peptide was washed with a solution of DMF/isopropanol (1:1) and dried with nitrogen.
Cleavage and Deprotection:
Cleavage was performed to detach the peptide molecule from its supportive resin and to remove the protective group. An acidolysis reaction was performed with 95% trifluoroacetic acid (TFA) with 5% water and 50 mg/mL dithioerythritol (DTE) as scavenger (10 mL TFA-based cleavage solution per gram of resin), e.g., for 3.25-3.5 hours at ambient temperature.

The resin was then filtered and rinsed twice with TFA in order to complete the extraction of the peptide.

The peptide solution volume was reduced under vacuum in a rotary evaporator (at about 35° C.) to a volume of about 30-35% of the original volume.

The peptide was then precipitated with a chilled mixture (−10±5° C.) of tert-butyl methyl ether (MTBE)/hexane (60:40 v/v) at a volume of 32 mL per gram resin.

The crude product was isolated by filtration, washed with MTBE and dried on the filter under a nitrogen stream to remove most of the solvent.

The obtained crude (linear) peptide was then solubilized in 90% acetic acid, the obtained solution was distributed in lyophilization flasks, shell frozen and lyophilized to dryness on a manifold lyophilizer, The peptide was analyzed by RP-HPLC for purity and by mass spectral analysis for confirmation of identity.
Oxidative Cyclization:
The crude linear peptide was cyclized by oxidation with hydrogen peroxide in a 0.1 M ammonium bicarbonate ($NH_4HCO_3$) solution, as follows:

The crude linear peptide was dissolved in 0.1 M $NH_4HCO_3$ at a concentration of 10 mg/mL, and an equal volume of 0.1 M $NH_4HCO_3$ was added to dilute the peptide to concentration of 5 mg/mL.

A solution of 1.5% hydrogen peroxide in water (5-fold excess) was then added dropwise to the peptide solution over a period of 25-30 minutes. The reaction was monitored using an Ellman test to confirm the absence of free sulfhydryl groups.

After completion of the reaction, the reaction mixture was acidified to pH 2-3 by addition of neat TFA and the resulting solution was used "as is" in the TEAP (triethylammonium phosphate) purification step.

First Preparative HPLC Columns (TEAP Purification):

The solution obtained upon completion of the cyclization step was purified by separation on a preparative RP-HPLC C18 column, 10 μm, 120 Å Daisogel™, loading about 2.4 L solution, containing about 11.7 grams crude peptide per kg resin.

The peptide was eluted with 0.1 M triethylammonium phosphate (TEAP) buffer (pH 2.25) and an acetonitrile (ACN) gradient. The gradient was as follows: 0% acetonitrile for 8 minutes, from 0% to 5% acetonitrile in 5 minutes (a rate of 1% per minute), and from 5% to 25% acetonitrile in 120 minutes (a rate of 0.17% per minute).

Elution fractions were collected, sampled and tested by HPLC to determine which fractions were pure enough (≥95%) to be pooled for the second chromatography purification step. Hydrophilic and hydrophobic fractions of the first RP-HPLC purification that do not meet the purity acceptance criterion are retained and may be re-processed to maximize overall yield.

Second Preparative HPLC Columns (Acetic Acid Purification):

Purified fractions obtained from TEAP injections were pooled, diluted 1:1 with water, and the peptide was separated on a 10 μm, 120 Å Daisogel™ C18 column, loaded at a volume of about 2.7 L per kg resin and eluted with a 35 mM acetic acid based buffer and acetonitrile gradient. The gradient was as follows: 0% acetonitrile for 8 minutes, and from 0% to 22% acetonitrile in 110 minutes (a rate of 0.2% per minute). The column was washed with four column volumes of 0.1 M ammonium acetate after loading of the peptide and prior to the start of the elution gradient to obtain the peptide as an acetate salt. Fraction collections were monitored by UV absorption at 230 nm.

The obtained composition contained BL-8040 (SEQ ID NO: 1) at a purity of 99.58% (i.e., peak area compared to the sum of all peak areas). Three additional peaks were detected: one at a relative retention time of 0.72, and at a concentration of 0.105%; another at a relative retention time of 0.87, and at a concentration of 0.108%; and a third one at a relative retention time of 0.91, identified as cyclic C-terminal-deamidated BL-8040 (SEQ ID NO: 2), and at a concentration of 0.055%. No other peaks of at least 0.05% were observed.

Example 2

Large Scale Phase Synthesis of BL-8040 According to Some Embodiments

The cyclic peptide BL-8040 (SEQ ID NO: 1) was prepared according to procedures described in Example 1. Peptide purity was evaluated by reverse phase high performance liquid chromatography (HPLC), using an Agilent™ 1200 HPLC system and Hypersil Gold™ C18 reverse phase column (250 mm length, 4.6 mm inner diameter, 5 μm particle size). Mobile phase A was 0.017 M perchloric acid ($HClO_4$) (pH 3) and mobile phase B was acetonitrile (100%), and a gradient of mobile phase B was from 19.4% to 29.4% in 50 minutes. The temperature was 40° C., the injection volume was 20 μl, the flow rate was 1 ml/minute, and detection was by absorption at a wavelength of 226 nm.

The product, BL-8040 (SEQ ID NO: 1), was detected at a retention time of 21.165 minutes (defined as relative retention time=1.00). An additional peak was detected at a retention time of 18.481 minutes, i.e., a relative retention time of 0.873, and at a concentration (i.e., peak area compared to the sum of all peak areas) of 0.148%. No other significant (i.e., ≥0.05%) peaks were observed.

The identity of BL-8040 (SEQ ID NO: 1) was confirmed by having essentially the same HPLC retention time as a reference sample of BL-8040 (SEQ ID NO: 1), as well as by Fourier transform infrared (FTIR) spectroscopy and amino acid analysis.

Analysis by mass spectrometry revealed the presence of a dominant ion peak with m/z value of 1080.3, which was identified as corresponding to $[M+2H]^{2+}$, where M is 2158.6 Da, which accords with the predicted molecular weight of BL-8040 (SEQ ID NO: 1).

Example 3

Large Scale Phase Synthesis of BL-8040 According to Some Embodiments

The cyclic peptide BL-8040 (SEQ ID NO: 1) was prepared according to procedures described in Example 1. Peptide purity was evaluated by reverse phase HPLC as described in Example 2, except that the pH of mobile phase A was 3.3 and the gradient of mobile phase B was from 19.8% to 29.8% in 50 minutes.

The product, BL-8040 (SEQ ID NO: 1), was detected at a retention time of 20.866 minutes (defined as relative retention time=1.00). Two additional peaks were observed: one at a retention time of 18.168 minutes, i.e., a relative retention time of 0.871, and at a concentration of 0.156%; and a smaller one at a retention time of 15.008 minutes, i.e., a relative retention time of 0.719, and at a concentration of 0.062%. No other significant (i.e., ≥0.05%) peaks were observed.

The identity of BL-8040 (SEQ ID NO: 1) was confirmed by having essentially the same HPLC retention time as a reference sample, as well as by Fourier transform infrared (FTIR) spectroscopy and amino acid analysis.

Analysis by mass spectrometry revealed the presence of two dominant ion peaks with m/z values of 1080.4 and 720.8, which were identified as corresponding to $[M+2H]^{2+}$ and $[M+3H]^{3+}$, where M is 2159 Da, which accords with the predicted molecular weight of BL-8040 (SEQ ID NO: 1).

The peptide was dissolved (with mannitol as excipient) in a buffered aqueous solution (pH 7). Peptide purity of evaluated by reverse phase HPLC according to procedures such as described herein (injection volume 20 μl), and reevaluated after 1, 3, 6, 9, 12, 18, 24 and 36 months of storage of the solution at 5±3° C. The abovementioned additional compounds were observed at a relative retention time of 0.88 (at a concentration of 0.15%) and at a relative retention time of 0.72 (at a concentration of 0.06%). No other significant (i.e., ≥0.05%) peaks were observed.

The concentration of each of the abovementioned compounds remained essentially unchanged over the course of 36 months. After 36 months, the concentration of the peak at 0.72 decreased very slightly to 0.14%, and an additional peak appeared at relative retention time of 0.97, with a concentration of 0.05%.

The absence of substantial change during storage indicates that the additional compounds characterized by relative retention times of about 0.72 and about 0.87 are associated with the process of preparing the BL-8040 (SEQ ID NO: 1) compound, rather than with degradation in solution.

Example 4

Large Scale Phase Synthesis of BL-8040 According to Some Embodiments

The cyclic peptide BL-8040 (SEQ ID NO: 1) was prepared according to procedures described in Example 1. Peptide purity was evaluated by reverse phase HPLC as described in Example 2, except that the gradient of mobile phase B was from 19.3% to 29.3% in 50 minutes.

The product, BL-8040 (SEQ ID NO: 1), was detected at a retention time of 20.675 minutes (defined as relative retention time=1.00). Three additional peaks were observed: two overlapping peaks at retention times of 17.911 and 17.999 minutes, i.e., relative retention times of 0.866 and 0.871, respectively, with concentrations of 0.10 and 0.13, respectively; and a third peak at a retention time of 22.223 minutes, i.e., a relative retention time of 1.075, and at a concentration of 0.05%. No other significant (i.e., ≥0.05%) peaks were observed.

Analysis by mass spectrometry revealed the presence of two dominant ion peaks with m/z values of 1080.3 and 720.8, which were identified as corresponding to $[M+2H]^{2+}$ and $[M+3H]^{3+}$, where M is 2159 Da, which accords with the predicted molecular weight of BL-8040 (SEQ ID NO: 1).

The peptide was dissolved (with mannitol as excipient) in a buffered aqueous solution (pH 7). Peptide purity of evaluated by reverse phase HPLC according to procedures such as described herein (injection volume 20 µl), and reevaluated after 1, 3, 6, 9, 12, 18 and 24 months of storage of the solution at 5±3° C. The abovementioned additional compounds were observed at a relative retention time of 0.87 (at a concentration of 0.23%), corresponding to the abovementioned overlapping peaks, and at a relative retention time of 1.09 (at a concentration of 0.05%), along with two additional peaks at a relative retention time of 0.72, and at a concentration of 0.05%, and at a relative retention time of 1.96, and at a concentration of 0.06%. No other significant (i.e., ≥0.05%) peaks were observed.

The concentration of the additional compounds characterized by relative retention times of 0.72 and 0.87 remained unchanged over the course of 24 months, whereas the concentration of the additional compounds characterized by relative retention times of 1.09 and 1.96 decreased to below 0.05%.

The absence of substantial change during storage indicates that the additional compounds characterized by relative retention times of about 0.72 and about 0.87 are associated with the process of preparing the BL-8040 (SEQ ID NO: 1) compound, rather than with degradation in solution.

Example 5

Large Scale Phase Synthesis of BL-8040 According to Some Embodiments

The cyclic peptide BL-8040 (SEQ ID NO: 1) was prepared according to procedures described in Example 1. Peptide purity was evaluated by reverse phase HPLC as described in Example 2, except that the gradient of mobile phase B was from 19.3% to 29.3% in 50 minutes.

The product, BL-8040 (SEQ ID NO: 1), was detected at a retention time of 21.000 minutes (defined as relative retention time=1.00). Two additional peaks were observed: one at a retention time of 18.268 minutes, i.e., a relative retention time of 0.870, and at a concentration of 0.22%; and a smaller one at a retention time of 15.252 minutes, i.e., a relative retention time of 0.726, and at a concentration of 0.05%. No other significant (i.e., ≥0.05%) peaks were observed.

The identity of BL-8040 (SEQ ID NO: 1) was confirmed by having essentially the same HPLC retention time as a reference sample, as well as by Fourier transform infrared (FTIR) spectroscopy and amino acid analysis.

Analysis by mass spectrometry revealed the presence of two dominant ion peaks with m/z values of 1080.4 and 720.8, which were identified as corresponding to $[M+2H]^{2+}$ and $[M+3H]^{3+}$, where M is 2159 Da, which accords with the predicted molecular weight of BL-8040 (SEQ ID NO: 1).

Additional liquid chromatography-mass spectrometry (LC/MS) analysis of the additional peak indicated the presence of two overlapping peaks, one compound characterized by a molecular weight of 2159 Da (possibly an isomer of BL-8040 (SEQ ID NO: 1)), and another compound characterized by a molecular weight of 2239 Da (about 80 Da above the molecular weight of BL-8040 (SEQ ID NO: 1)).

In view of the above, the peak at a relative retention time of 0.870 was determined to comprise two overlapping peaks, one with a retention time of 18.26 minutes and concentration of 0.10%, and another with a retention time of 18.27 minutes and concentration of 0.12%.

The peptide was dissolved (with mannitol as excipient) in a buffered aqueous solution (pH 7). Peptide purity of the solution was evaluated by reverse phase HPLC, according to procedures described herein (injection volume 20 µl), and reevaluated after 6, 12 and 24 months of storage of the solution at 5±3° C. The abovementioned additional compounds were observed at a relative retention time of 0.87 (at a concentration of 0.21%), corresponding to the abovementioned overlapping peaks, and at a relative retention time of 0.72 (at a concentration of 0.05%. No other significant (i.e., ≥0.05%) peaks were observed. The concentration of the additional compounds remained unchanged over the course of 24 months.

The absence of substantial change during storage indicates that the compounds characterized by relative retention times of about 0.72 and about 0.87 are associated with the process of preparing the BL-8040 (SEQ ID NO: 1) compound, rather than with degradation in solution.

Example 6

Large Scale Phase Synthesis of BL-8040 According to Some Embodiments

The cyclic peptide BL-8040 (SEQ ID NO: 1) was prepared according to procedures described in Example 1. Peptide purity was evaluated by reverse phase HPLC as described in Example 2, except that the gradient of mobile phase B was from 20% to 30% in 50 minutes, the injection volume was 5 µl, and an Agilent™ 1100 HPLC system was used.

The product, BL-8040 (SEQ ID NO: 1), was detected at a retention time of 22.421 minutes (defined as relative retention time=1.00). An additional peak was observed at a retention time of 19.635 minutes, i.e., a relative retention time of 0.876, and at a concentration of 0.10%. No other significant (i.e., ≥0.05%) peaks were observed.

The peptide was dissolved (with mannitol as excipient) in a buffered aqueous solution (pH 7), in two batches. Peptide purity of the solutions was evaluated by reverse phase HPLC, according to procedures described herein (injection volume 20 μl). In one batch, the abovementioned additional compound was observed at a relative retention time of 0.87, at a concentration of 0.10%. In the other batch, the abovementioned compound was observed at a relative retention time of 0.87, at a concentration of 0.11%; along with an additional peak at a relative retention time of 0.92, and at a concentration of 0.05%, which was attributed to cyclic deamidated BL-8040 (SEQ ID NO: 2). No other significant (i.e., ≥0.05%) peaks were observed.

Example 7

Large Scale Phase Synthesis of BL-8040 According to Some Embodiments

The cyclic peptide BL-8040 (SEQ ID NO: 1) was prepared according to procedures described in Example 1. Peptide purity was evaluated by reverse phase HPLC as described in Example 6.

The product, BL-8040 (SEQ ID NO: 1), was detected at a retention time of 22.035 minutes (defined as relative retention time=1.00). Two additional peaks were observed: one at a retention time of 19.259 minutes, i.e., a relative retention time of 0.874, and at a concentration of 0.08%; and another one at a retention time of 15.845 minutes, i.e., a relative retention time of 0.719, and at a concentration of 0.11%. No other significant (i.e., ≥0.05%) peaks were observed.

The peptide was dissolved (with mannitol as excipient) in a buffered aqueous solution (pH 7), in two batches. Peptide purity of the solutions was evaluated by reverse phase HPLC, according to procedures described herein (injection volume 20 μl). The abovementioned additional compounds were observed at a relative retention time of 0.87 (at a concentration of 0.08%) and at a relative retention time of 0.72 (at a concentration of 0.11%). No other significant (i.e., ≥0.05%) peaks were observed.

Peptide purity of one of the batches was reevaluated after 3, 6, 9 and 12 months of storage at 5±3° C. The concentration of each of the abovementioned additional compounds remained essentially unchanged over the course of 12 months.

The absence of substantial change during storage indicates that the compounds characterized by relative retention times of about 0.72 and about 0.87 are associated with the process of preparing the BL-8040 (SEQ ID NO: 1) compound, rather than with degradation in solution.

Reference Example

Solid Phase Synthesis of BL-8040

BL-8040 (SEQ ID NO: 1) was prepared by solid phase peptide synthesis on a Rink amide resin, in 5 different lots. HOBt/TBTU (tetrafluoroborate benzotriazole uronium derivative of hydroxybenzotriazole) with organic base (DIPEA or collidine) in DMF was used as coupling reagents, and acetic anhydride was used for capping by acetylation. The synthesized peptide was cleaved from the resin using trifluoroacetic acid (TFA), dodecyl-mercaptan (DDM), water and triisopropylsilane (TIS), and precipitated in MTBE (methyl tert-butyl ether). The obtained linear peptide then purified by reverse phase HPLC with gradient of 0.1% trifluoroacetic acid and acetonitrile; the collected fractions were concentrated and cyclization of the peptide was then effected by oxidation using iodine in acetic acid.

The peptide purity (for each of the 5 lots) was evaluated by reverse phase HPLC with gradient of 0.1% trifluoroacetic acid and acetonitrile, followed by reverse phase HPLC with acetic acid buffer.

The purity of BL-8040 (SEQ ID NO: 1) in each lot was in a range of from 96.70% to 99.28%. Prominent additional compounds included cyclic C-terminal-deamidated BL-8040 (SEQ ID NO: 2), which was characterized by a relative retention time of 0.91 and present at a concentration in a range of from 0.259% to 0.373% in 4 of the 5 lots; and cyclic BL-8040 with acetylated D-Lys (SEQ ID NO: 3), which was characterized by a relative retention time of 1.10 and present at a concentration in a range of from 0.054% to 0.223% in 4 of the 5 lots.

An additional compound characterized by a relative retention time of 0.86-0.88 was detected in 3 of the 5 lots, at a concentration representing from 4% to 15% of total compounds other than BL-8040 (SEQ ID NO: 1). An additional compound characterized by a relative retention time of 0.71-0.73 was detected in only one of the 5 lots, at a concentration representing only 2% of total compounds other than BL-8040 (SEQ ID NO: 1).

Example 8

Effect on In Vivo Neutrophil Migration of Compositions Comprising BL-8040

BL-8040 (SEQ ID NO: 1) is an antagonist of the CXCR4 chemokine receptor. The induction of the cellular activity mediated by CXCR4 is responsible for the attachment of white blood cells to the bone marrow stromal cells. Inhibition of the CXCR4 activity (e.g., by BL-8040 (SEQ ID NO: 1)) is therefore expected to induce the detachment of the white blood cells (which include but are not limited to neutrophils) from the bone marrow stroma, and the subsequent migration of the cells to the peripheral blood.

The biological activity of compositions comprising BL-8040 (SEQ ID NO: 1), prepared as described in Example 1 and Reference Example 1, was compared by evaluating migration of neutrophils to peripheral blood after injection.

Mice were subcutaneously injected with a single dose of 5 mg/kg of BL-8040 (SEQ ID NO: 1), reconstituted in 200 μl of PBS. The mice were bled 2 hours after BL-8040 (SEQ ID NO: 1) injection by cardiac puncture into tubes with heparin. Flow cytometry was used to evaluate the number of mature neutrophils in the peripheral blood, and the increase relative to control mice was calculated.

As shown in Table 1, the presence (alongside BL-8040 (SEQ ID NO: 1)) of compounds with retention times of about 0.87 and 0.72 was correlated with a stronger biological activity, as determined by evaluating neutrophil migration.

TABLE 1

Effect of BL-8040 (SEQ ID NO: 1) compositions prepared by different techniques, with and without compounds having relative retention times (RRT) of 0.87 and 0.72, on neutrophil migration to peripheral blood after injection

| Synthesis of BL-8040 (SEQ ID NO: 1) | Fold increase in neutrophil number | RRT = 0.87 | RRT = 0.72 |
|---|---|---|---|
| Example 1 | 9.9 | 0.108% | 0.105% |
| Reference Example 1 | 5.6 | <0.05% | <0.05% |

Example 9

Inhibition of CXCL12-Induced Breast Cancer Cell Migration by Compositions Comprising BL-8040

The inhibitory activity of BL-8040 (SEQ ID NO: 1) compositions towards CXCL12-induced breast cancer cell migration is evaluated, as CXCL12 is a natural ligand of CXCR4 (optionally using procedures such as described in U.S. Pat. No. 7,423,007). The inhibitory activity of a BL-8040 (SEQ ID NO: 1) composition which includes compounds with retention times of about 0.87 and 0.72 (optionally prepared as described in any of Examples 1-7) is compared with that of a BL-8040 (SEQ ID NO: 1) composition which lacks such compounds with retention times of about 0.87 and 0.72 (optionally prepared as described in Reference Example 1).

A Transwell® insert is treated (optionally at 37° C. for 6 hours) with a fibronectin solution (optionally about 10 μg/ml) and dried, and then CXCL12 (optionally 100 nM) and cell growth medium (optionally 600 μl of DMEM with 0.1% bovine serum albumin) with the BL-8040 (SEQ ID NO: 1) composition is added to the lower chamber of a Transwell® plate. The tested BL-8040 (SEQ ID NO: 1) composition and breast cancer cells (optionally MDA-MB-231 cells at $2 \times 10^6$ cells/ml) and cell growth medium (optionally 100 μl of DMEM with 0.1% bovine serum albumin) are added to the upper chamber. After incubation (optionally for about 15 hours at 37° C. in the presence of 5% $CO_2$) cells on the lower surface of the well are quantified, optionally by fixing and staining (e.g., with 25% methanol and 0.5% crystal violet), and compared to a control sample with no BL-8040 (SEQ ID NO: 1).

Example 10

Inhibition of CXCL12-Induced Leukemia Cell Migration by Compositions Comprising BL-8040

The inhibitory activity of BL-8040 (SEQ ID NO: 1) compositions towards CXCL12-induced T-cell-derived leukemia cell migration is evaluated (optionally using procedures such as described in U.S. Pat. No. 7,423,007). The inhibitory activity of a BL-8040 (SEQ ID NO: 1) composition which includes compounds with retention times of about 0.87 and 0.72 (optionally prepared as described in any of Examples 1-7) is compared with that of a BL-8040 (SEQ ID NO: 1) composition which lacks such compounds with retention times of about 0.87 and 0.72 (optionally prepared as described in Reference Example 1).

CXCL12 (optionally 30 nM) and cell growth medium (optionally 600 μl of DMEM with 0.1% bovine serum albumin) with the BL-8040 (SEQ ID NO: 1) composition is added to the lower chamber of a Transwell® plate. The tested BL-8040 (SEQ ID NO: 1) composition and leukemia cells (optionally SUP-T1 cells at $2 \times 10^6$ cells/ml) and cell growth medium (optionally 100 μl of DMEM with 0.1% bovine serum albumin) are added to the upper chamber. After incubation (optionally for about 4 hours at 37° C. in the presence of 5% $CO_2$) the mount of cells which moved to the lower chamber is quantified, optionally using a Coulter counter, and compared to a control sample with no BL-8040 (SEQ ID NO: 1).

Example 11

Anti-Metastatic Activity of Compositions Comprising BL-8040 in Animal Model

The ability of BL-8040 (SEQ ID NO: 1) compositions to inhibit metastatic breast cancer cell migration is evaluated in an animal model (optionally using procedures such as described in U.S. Pat. No. 7,423,007). The inhibitory activity of a BL-8040 (SEQ ID NO: 1) composition which includes compounds with retention times of about 0.87 and 0.72 (optionally prepared as described in any of Examples 1-7) is compared with that of a BL-8040 (SEQ ID NO: 1) composition which lacks such compounds with retention times of about 0.87 and 0.72 (optionally prepared as described in Reference Example 1).

Breast cancer cells (optionally $10^6$ MDA-MB-231 human breast cancer cells) are implanted intravenously into the tails of mice (optionally five week-old female CB-17 SCID mice). A BL-8040 (SEQ ID NO: 1) composition comprising physiological saline (optionally adjusted to a BL-8040 (SEQ ID NO: 1) concentration of 80 mg/ml) is administered gradually (optionally over the course of four weeks) to the mice (optionally using sustained-release osmotic pumps, to administer about 18.2 mg/kg/day).

The amount of cancer cells in the lungs of the mice is then evaluated, optionally using Evan's Blue solution (e.g., 0.2%, 2 ml) injected through the windpipes followed by soaking the lungs in Bouin's liquid, staining, fixing, and observing metastatic focus (yellow-stained potion), and compared to a control sample with no BL-8040 (SEQ ID NO: 1).

Example 12

Effect of Compositions Comprising BL-8040 on Delayed-Type Hypersensitivity (DTH) Reaction in Animal Model The ability of BL-8040 (SEQ ID NO: 1) compositions to inhibit a delayed-type hypersensitivity (DTH) reaction is evaluated in an animal model (optionally using procedures such as described in U.S. Pat. No. 7,423,007). The inhibitory activity of a BL-8040 (SEQ ID NO: 1) composition which includes compounds with retention times of about 0.87 and 0.72 (optionally prepared as described in any of Examples 1-7) is compared with that of a BL-8040 (SEQ ID NO: 1) composition which lacks such compounds with retention times of about 0.87 and 0.72 (optionally prepared as described in Reference Example 1).

Sheep red blood cells suspended in physiological saline solution (optionally $2 \times 10^7$ cells per 50 μl) are administered subcutaneously (optionally to the ankles of the left hind limbs) of mice (optionally 6 week-old male BALB/c mice). After 5 days, a larger dose of sheep red blood cells (optionally $10^8$ cells per 50 μl) are administered subcutaneously at a second location in the mice (optionally to the ankles of the right hind limbs) and the DTH reaction is induced. Immediately prior to and about 24 hours after the induction of antigens, the inflammation at the second location is quantified (e.g., by determining ankle thickness) and used as a quantitative indicator of DTH.

A BL-8040 (SEQ ID NO: 1) composition comprising PBS is administered gradually to the mice (optionally using sustained-release osmotic pumps, to administer about 4, about 8, about 24 and/or about 120 μg/day), beginning on the day before sensitization. The DTH reaction with BL-8040 (SEQ ID NO: 1) composition is then compared with the DTH reaction of control mice to whom BL-8040 (SEQ ID NO: 1) is not administered.

Example 13

Effect of Compositions Comprising BL-8040 on Collagen-Induced Arthritis in Animal Model The ability of BL-8040 (SEQ ID NO: 1) compositions to inhibit development of collagen-induced arthritis is evaluated in an animal model (optionally using procedures such as described in U.S. Pat. No. 7,423,007). The inhibitory activity of a BL-8040 (SEQ ID NO: 1) composition which includes compounds with retention times of about 0.87 and 0.72 (optionally prepared as described in any of Examples 1-7) is compared with that of a BL-8040 (SEQ ID NO: 1) composition which lacks such compounds with retention times of about 0.87 and 0.72 (optionally prepared as described in Reference Example 1).

Bovine type II collagen is dissolved (optionally at 2 mg/ml) in an acetic acid (optionally 0.05 M) solution, and an emulsion is prepared with an equal volume of FCA (Freund's complete adjuvant). The emulsion (optionally 50 µl) is injected intradermally (optionally at the base of the tail) to mice (optionally 6 week-old male DBA/1JN mice), and sensitized later (optionally about 21 days after the injection) by a similar immunization. After the second immunization (optionally for about two weeks), body weight and/or hind limb thickness is measured and arthritis scoring is performed. Arthritis is optionally scored at 0-3 points of each limb, and evaluated by the total of the same (12 points being the full points; 0=normal; 1=mild swelling or swelling of a single digit; 2=moderate swelling or swelling of plural digits; 3=severe swelling). At the end of this time period (optionally two weeks), four limbs and sera are picked.

Type II collagen-specific antibodies (e.g., IgG2a antibodies) are then quantified using any suitable technique, optionally by the following procedures: after coat blocking bovine type II collagen (e.g., 10 µg/ml in PBS solution) on an immunoplate, ×1000 diluted mouse serum (e.g., 100 µl) is added and kept at room temperature (e.g., for about 2 hours); after cleansing, anti-mouse IgG2a antibody (×1000 dilution) is added; after cleansing, TMB is added and kept at room temperature (e.g., for about 30 minutes), an equal amount of $H_2SO_4$ is added, and absorption is determined at about 450 nm.

A BL-8040 (SEQ ID NO: 1) composition comprising PBS is administered gradually (optionally over the course of two weeks) to the mice (optionally using sustained-release osmotic pumps, to administer about 0.5 µl per hour), beginning on the day before the second immunization.

The arthritis score, body weight loss and/or collagen-specific antibody levels upon administration of BL-8040 (SEQ ID NO: 1) composition is then compared with that of control mice to whom BL-8040 (SEQ ID NO: 1) is not administered.

Example 14

Effect of Compositions Comprising BL-8040 on CXCL12 Binding to CXCR4

The ability of BL-8040 (SEQ ID NO: 1) compositions to inhibit binding of CXCL12 to CXCR4 is evaluated in cells in vitro (optionally using procedures such as described in U.S. Pat. No. 7,423,007). The inhibitory activity of a BL-8040 (SEQ ID NO: 1) composition which includes compounds with retention times of about 0.87 and 0.72 (optionally prepared as described in any of Examples 1-7) is compared with that of a BL-8040 (SEQ ID NO: 1) composition which lacks such compounds with retention times of about 0.87 and 0.72 (optionally prepared as described in Reference Example 1).

Radioactive-labeled CXCL12 (optionally 200 pM of $^{125}$I-CXCL120) is used for quantifying binding of CXC12 to CXCR4 in cells expressing CXCR4 (optionally Jurkat human T-cell leukemia cells). Optionally, 50 µl of Jurkat cells ($6 \times 10^6$ cells/ml) are suspended in buffer (Dulbecco's PBS solution, pH 7.0, containing 0.5% bovine serum albumin and 20 mM HEPES), 25 µl of tested BL-8040 composition diluted by buffer and 25 µl of a solution of the radio-labeled CXCL12 are respectively dispensed to various wells of a plate, and subjected to fixation reaction for 1 hour at room temperature, followed by determining each well's radioactivity.

Control samples with no BL-8040 (SEQ ID NO: 1) may serve to represent no binding inhibition, and control samples with non-radio-labeled CXCL12 (optionally 100 nM) may serve to represent complete binding inhibition.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A composition-of-matter comprising BL-8040 (SEQ ID NO: 1) and at least one compound characterized by a relative retention time in a range of from 0.86 to 0.88, wherein said relative retention time is determined using a first mobile phase which is an aqueous solution of 0.017 M perchlorate at a pH in a range of from about 3.0 to about 3.3, a second mobile phase which is acetonitrile, a gradient whereby a concentration of said second mobile phase increases by about 10% in about 50 minutes from an initial concentration of about 20%, a C18 reverse phase column, an injection volume in a range of from about 5 to about 20 µl, and a flow rate of about 1 ml per minute, at a temperature of about 40° C., and wherein a relative retention time of said BL-8040 (SEQ ID NO: 1) is defined as 1, the composition-of-matter being produced by a process of preparing said BL-8040 (SEQ ID NO: 1) which comprises:

(a) sequentially coupling amino acids and 4-fluorobenzoic acid to a resin by solid phase peptide synthesis, thereby obtaining a linear peptide coupled to said resin;

(b) cleaving said linear peptide from said resin, thereby obtaining a free linear peptide;

(c) oxidizing cysteine residues of said linear peptide to form an intramolecular disulfide bond, thereby obtaining the cyclic peptide having SEQ ID NO: 1 in solution; and (d) isolating the cyclic peptide having SEQ ID NO: 1, or a pharmaceutically acceptable salt thereof.

2. The composition-of-matter of claim 1, wherein said at least one compound represents at least 20% of all compounds other than BL-8040 (SEQ ID NO: 1) in the composition-of-matter as determined according to absorption at a wavelength at about 226 nm.

3. The composition-of-matter of claim 1, wherein a total concentration ratio of said at least one compound to said BL-8040 (SEQ ID NO: 1) is at least about 0.01% and/or is no more than about 1%.

4. The composition-of-matter of claim 1, further comprising at least one compound characterized by a relative retention time in a range of from 0.71 to 0.73.

5. The composition-of-matter of claim 4, wherein said at least one compound characterized by a relative retention time in a range of from 0.71 to 0.73 represents at least 10% of all compounds other than BL-8040 (SEQ ID NO: 1) in the composition-of-matter as determined according to absorption at a wavelength at about 226 nm.

6. The composition-of-matter of claim 4, wherein a total concentration ratio of said at least one compound characterized by a relative retention time in a range of from 0.71 to 0.73 to said BL-8040 (SEQ ID NO: 1) is at least about 0.01% and/or is in a range of from about 0.03% to about 0.15%.

7. The composition-of-matter of claim 4, wherein a total concentration of said at least one compound characterized by a relative retention time in a range of from 0.86 to 0.88 and said at least one compound characterized by a relative retention time in a range of from 0.71 to 0.73 represents at least 50% of all compounds other than BL-8040 (SEQ ID NO: 1) in the composition-of-matter as determined according to absorption at a wavelength at about 226 nm.

8. A composition-of-matter comprising BL-8040 (SEQ ID NO: 1) and at least one compound characterized by a relative retention time in a range of from 0.86 to 0.88, wherein a total concentration ratio of said at least one compound to said BL-8040 (SEQ ID NO: 1) is in a range of from 0.075% to 0.225% as determined according to absorption at a wavelength at about 226 nm,
wherein said relative retention time is determined using a first mobile phase which is an aqueous solution of 0.017 M perchlorate at a pH in a range of from about 3.0 to about 3.3, a second mobile phase which is acetonitrile, a gradient whereby a concentration of said second mobile phase increases by about 10% in about 50 minutes from an initial concentration of about 20%, a C18 reverse phase column, an injection volume in a range of from about 5 to about 20 µl, and a flow rate of about 1 ml per minute, at a temperature of about 40° C., and wherein a relative retention time of said BL-8040 (SEQ ID NO: 1) is defined as 1,
the composition-of-matter being produced by a process of preparing said BL-8040 (SEQ ID NO: 1) which comprises:
(a) sequentially coupling amino acids and 4-fluorobenzoic acid to a resin by solid phase peptide synthesis, thereby obtaining a linear peptide coupled to said resin;
(b) cleaving said linear peptide from said resin, thereby obtaining a free linear peptide;
(c) oxidizing cysteine residues of said linear peptide to form an intramolecular disulfide bond, thereby obtaining the cyclic peptide having SEQ ID NO: 1 in solution; and
(d) isolating the cyclic peptide having SEQ ID NO: 1, or a pharmaceutically acceptable salt thereof.

9. A composition-of-matter comprising BL-8040 (SEQ ID NO: 1) and at least one compound characterized by a relative retention time in a range of from 0.71 to 0.73, said at least one compound representing at least 10% of all compounds other than BL-8040 (SEQ ID NO: 1) in the composition-of-matter as determined according to absorption at a wavelength at about 226 nm,
wherein said relative retention time is determined using a first mobile phase which is an aqueous solution of 0.017 M perchlorate at a pH in a range of from about 3.0 to about 3.3, a second mobile phase which is acetonitrile, a gradient whereby a concentration of said second mobile phase increases by about 10% in about 50 minutes from an initial concentration of about 20%, a C18 reverse phase column, an injection volume in a range of from about 5 to about 20 µl, and a flow rate of about 1 ml per minute, at a temperature of about 40° C., and wherein a relative retention time of said BL-8040 (SEQ ID NO: 1) is defined as 1,
the composition-of-matter being produced by a process of preparing said BL-8040 (SEQ ID NO: 1) which comprises:
(a) sequentially coupling amino acids and 4-fluorobenzoic acid to a resin by solid phase peptide synthesis, thereby obtaining a linear peptide coupled to said resin;
(b) cleaving said linear peptide from said resin, thereby obtaining a free linear peptide;
(c) oxidizing cysteine residues of said linear peptide to form an intramolecular disulfide bond, thereby obtaining the cyclic peptide having SEQ ID NO: 1 in solution; and
(d) isolating the cyclic peptide having SEQ ID NO: 1, or a pharmaceutically acceptable salt thereof.

10. The composition-of-matter of claim 9, wherein a total concentration ratio of said at least one compound to said BL-8040 (SEQ ID NO: 1) is at least about 0.01% and/or is no more than about 0.5%.

11. The composition-of-matter of claim 9, further comprising at least one compound characterized by a relative retention time in a range of from 0.86 to 0.88.

12. The composition-of-matter of claim 11, wherein a total concentration ratio of said at least one compound characterized by a relative retention time in a range of from 0.86 to 0.88 to said BL-8040 (SEQ ID NO: 1) is at least about 0.01% and/or is in a range of from about 0.075% to about 0.225%.

13. The composition-of-matter of claim 11, wherein a total concentration of said at least one compound characterized by a relative retention time in a range of from 0.86 to 0.88 and said at least one compound characterized by a relative retention time in a range of from 0.71 to 0.73 represents at least 50% of all compounds other than BL-8040 (SEQ ID NO: 1) in the composition-of-matter as determined according to absorption at a wavelength at about 226 nm.

14. The composition-of-matter of claim 1,
wherein:
(i) said coupling is effected using diisopropylcarbodiimide (DIC) in combination with ethyl cyanohydroxyiminoacetate and/or N-hydroxybenzotriazole;
(ii) said cleaving is effected by contacting said linear peptide coupled to said resin with a solution comprising trifluoroacetic acid (TFA) and a scavenger selected from the group consisting of dithioerythritol (DTE) and dithiothreitol (DTT);
(iii) the process further comprises precipitating said free linear peptide after said cleaving without concentrating said free linear peptide by evaporation prior to said precipitating;
(iv) said contacting is effected by contacting an aqueous solution comprising said linear peptide at a concentration of at least 5 mg/mL with hydrogen peroxide;
(v) said isolating comprises loading said cyclic peptide on a reverse phase chromatography column at a concentration of no more than 40 grams cyclic peptide per kg of said column, and eluting said cyclic peptide from said column;
(vi) said isolating the cyclic peptide having SEQ ID NO: 1 comprises lyophilization, and the process further comprises grinding said cyclic peptide following said lyophilization; and/or
(vii) a degree of substitution of said resin is at least 0.3 milliequivalents per gram, and/or said resin is a Rink aminomethylstyrene resin.

15. The composition-of-matter of claim 1, characterized by enhanced promotion of in vivo neutrophil migration to peripheral blood, relative to a corresponding composition-of-matter lacking a compound characterized by a relative retention time in a range of from 0.71 to 0.73 and a compound characterized by a relative retention time in a range of from 0.86 to 0.88.

16. A pharmaceutical composition comprising the composition-of-matter of claim 1, and a pharmaceutically acceptable carrier.

17. A method of treating a condition treatable by BL-8040 (SEQ ID NO: 1) and/or a condition in which inhibiting CXCR4 is advantageous and/or a condition selected from the group consisting of retinoblastoma, neuroectodermal derived tumors, large cell lung cancer, multiple myeloma, microglioma, glioma, breast cancer, pancreatic cancer, thrombocytopenia, risk of bone marrow suppression, and HIV infection in a subject in need thereof, the method comprising administering to the subject the composition-of-matter of claim 1, thereby treating the condition.

18. The composition-of-matter of claim 9,
wherein:
(i) said coupling is effected using diisopropylcarbodiimide (DIC) in combination with ethyl cyanohydroxyiminoacetate and/or N-hydroxybenzotriazole;
(ii) said cleaving is effected by contacting said linear peptide coupled to said resin with a solution comprising trifluoroacetic acid (TFA) and a scavenger selected from the group consisting of dithioerythritol (DTE) and dithiothreitol (DTT);
(iii) the process further comprises precipitating said free linear peptide after said cleaving without concentrating said free linear peptide by evaporation prior to said precipitating;
(iv) said contacting is effected by contacting an aqueous solution comprising said linear peptide at a concentration of at least 5 mg/mL with hydrogen peroxide;
(v) said isolating comprises loading said cyclic peptide on a reverse phase chromatography column at a concentration of no more than 40 grams cyclic peptide per kg of said column, and eluting said cyclic peptide from said column;
(vi) said isolating the cyclic peptide having SEQ ID NO: 1 comprises lyophilization, and the process further comprises grinding said cyclic peptide following said lyophilization; and/or
(vii) a degree of substitution of said resin is at least 0.3 milliequivalents per gram, and/or said resin is a Rink aminomethylstyrene resin.

19. The composition-of-matter of claim 9, characterized by enhanced promotion of in vivo neutrophil migration to peripheral blood, relative to a corresponding composition-of-matter lacking a compound characterized by a relative retention time in a range of from 0.71 to 0.73 and a compound characterized by a relative retention time in a range of from 0.86 to 0.88.

20. A pharmaceutical composition comprising the composition-of-matter of claim 9, and a pharmaceutically acceptable carrier.

21. A method of treating a condition treatable by BL-8040 (SEQ ID NO: 1) and/or a condition in which inhibiting CXCR4 is advantageous and/or a condition selected from the group consisting of retinoblastoma, neuroectodermal derived tumors, large cell lung cancer, multiple myeloma, microglioma, glioma, breast cancer, pancreatic cancer, thrombocytopenia, risk of bone marrow suppression, and HIV infection in a subject in need thereof, the method comprising administering to the subject the composition-of-matter of claim 9, thereby treating the condition.

22. The composition-of-matter of claim 1, wherein said at least one compound characterized by a relative retention time in a range of from 0.86 to 0.88 comprises a compound having the same molecular weight as BL-8040 (SEQ ID NO: 1) and/or a compound having a molecular weight which is higher than the molecular weight of BL-8040 (SEQ ID NO: 1) by no more than 100 Da, said molecular weight being determined by mass spectrometry.

23. The composition-of-matter of claim 8, wherein said at least one compound characterized by a relative retention time in a range of from 0.86 to 0.88 comprises a compound having the same molecular weight as BL-8040 (SEQ ID NO: 1) and/or a compound having a molecular weight which is higher than the molecular weight of BL-8040 (SEQ ID NO: 1) by no more than 100 Da, said molecular weight being determined by mass spectrometry.

24. The composition-of-matter of claim 1, wherein said process is a large-scale process of preparing in a single run of the process at least 100 grams of BL-8040 (SEQ ID NO: 1).

25. The composition-of-matter of claim 8, wherein said process is a large-scale process of preparing in a single run of the process at least 100 grams of BL-8040 (SEQ ID NO: 1).

26. The composition-of-matter of claim 9, wherein said process is a large-scale process of preparing in a single run of the process at least 100 grams of BL-8040 (SEQ ID NO: 1).

* * * * *

SEQUENCE LISTING

```
Sequence total quantity: 3
SEQ ID NO: 1            moltype = AA  length = 14
FEATURE                 Location/Qualifiers
REGION                  1..14
                        note = synthetic peptide
MOD_RES                 1
                        note = 4-fluorobenzoyl-arginine
MOD_RES                 3
                        note = 3-((2-naphthyl) alanine
MOD_RES                 6
                        note = citrulline
MOD_RES                 8
                        note = D-lysine
MOD_RES                 12
                        note = citrulline
```

```
MOD_RES              14
                     note = C' AMIDATED
source               1..14
                     mol_type = protein
                     organism = synthetic construct
SEQUENCE: 1
RRACYRKKPY RRCR                                                                    14

SEQ ID NO: 2         moltype = AA  length = 14
FEATURE              Location/Qualifiers
REGION               1..14
                     note = synthetic peptide
MOD_RES              1
                     note = 4-fluorobenzoyl-arginine
MOD_RES              3
                     note = 3-((2-naphthyl) alanine
MOD_RES              6
                     note = citrulline
MOD_RES              8
                     note = D-lysine
MOD_RES              12
                     note = citrulline
source               1..14
                     mol_type = protein
                     organism = synthetic construct
SEQUENCE: 2
RRACYRKKPY RRCR                                                                    14

SEQ ID NO: 3         moltype = AA  length = 14
FEATURE              Location/Qualifiers
REGION               1..14
                     note = synthetic peptide
MOD_RES              1
                     note = 4-fluorobenzoyl-arginine
MOD_RES              3
                     note = 3-((2-naphthyl) alanine
MOD_RES              6
                     note = citrulline
MOD_RES              8
                     note = N-acetyl D-lysine
MOD_RES              12
                     note = citrulline
MOD_RES              14
                     note = C' AMIDATED
source               1..14
                     mol_type = protein
                     organism = synthetic construct
SEQUENCE: 3
RRACYRKKPY RRCR                                                                    14
```